United States Patent
Simmons et al.

(10) Patent No.: US 9,011,560 B2
(45) Date of Patent: Apr. 21, 2015

(54) VARIOUS METHODS AND APPARATUSES FOR AN ULTRA-HIGH HEAT FLUX CHEMICAL REACTOR

(75) Inventors: Wayne W. Simmons, Dublin, OH (US); Christopher Perkins, Boulder, CO (US); Zoran Jovanovic, Louisville, CO (US); Courtland M. Hilton, Broomfield, CO (US); Peter Popp, Broomfield, CO (US); Bryan J. Schramm, Broomfield, CO (US); John T. Turner, West Chester, OH (US)

(73) Assignee: Sundrop Fuels, Inc., Longmont, CO (US)

( * ) Notice: Subject to any disclaimer, the term of this patent is extended or adjusted under 35 U.S.C. 154(b) by 115 days.

(21) Appl. No.: 13/254,020

(22) PCT Filed: Dec. 8, 2010

(86) PCT No.: PCT/US2010/059564
§ 371 (c)(1),
(2), (4) Date: Aug. 31, 2011

(87) PCT Pub. No.: WO2011/155962
PCT Pub. Date: Dec. 15, 2011

(65) Prior Publication Data
US 2012/0145965 A1    Jun. 14, 2012

Related U.S. Application Data

(63) Continuation-in-part of application No. 12/795,947, filed on Jun. 8, 2010.

(60) Provisional application No. 61/380,116, filed on Sep. 3, 2010, provisional application No. 61/248,282, filed on Oct. 2, 2009, provisional application No. 61/185,492, filed on Jun. 9, 2009.

(51) Int. Cl.
*B01J 7/00*    (2006.01)
*C07C 29/152*    (2006.01)
(Continued)

(52) U.S. Cl.
CPC ............... *C07C 29/152* (2013.01); *C01B 3/24* (2013.01); *C01B 3/34* (2013.01); *C10J 3/485* (2013.01);
(Continued)

(58) Field of Classification Search
USPC .......................................................... 48/61
See application file for complete search history.

(56) References Cited

U.S. PATENT DOCUMENTS 2,237,491 A    4/1941    Kutz
6,402,988 B1    6/2002    Gottzmann et al.
(Continued)

FOREIGN PATENT DOCUMENTS

WO    WO/2010/144554 A1    12/2010
WO    WO/2011/155962 A1    12/2011

OTHER PUBLICATIONS

Notification Concerning Transmittal of International Preliminary Report on Patentability for International Application No. PCT/US2010/059564, mailed Dec. 20, 2012, 10 pages, The International Bureau of WIPO, Geneva, Switzerland.
(Continued)

*Primary Examiner* — Matthew Merkling
(74) *Attorney, Agent, or Firm* — Rutan & Tucker, LLP

(57) ABSTRACT

Various processes and apparatus are discussed for an ultra-high heat flux chemical reactor. A thermal receiver and the reactor tubes are aligned to 1) absorb and re-emit radiant energy, 2) highly reflect radiant energy, and 3) any combination of these, to maintain an operational temperature of the enclosed ultra-high heat flux chemical reactor. Particles of biomass are gasified in the presence of a steam carrier gas and methane in a simultaneous steam reformation and steam biomass gasification reaction to produce reaction products that include hydrogen and carbon monoxide gas using the ultra-high heat flux thermal energy radiated from the inner wall and then into the multiple reactor tubes. The multiple reactor tubes and cavity walls of the receiver transfer energy primarily by radiation absorption and re-radiation, rather than by convection or conduction, to the reactants in the chemical reaction to drive the endothermic chemical reaction flowing in the reactor tubes.

13 Claims, 8 Drawing Sheets

(51) Int. Cl.
  *C01B 3/24* (2006.01)
  *C01B 3/34* (2006.01)
  *C10J 3/48* (2006.01)
  *C10J 3/50* (2006.01)
  *C10J 3/84* (2006.01)
  *F28D 21/00* (2006.01)

(52) U.S. Cl.
  CPC .. *C10J 3/506* (2013.01); *C10J 3/84* (2013.01); *C01B 2203/0216* (2013.01); *C01B 2203/0222* (2013.01); *C01B 2203/0272* (2013.01); *C01B 2203/0485* (2013.01); *C01B 2203/0495* (2013.01); *C01B 2203/061* (2013.01); *C01B 2203/062* (2013.01); *C01B 2203/0816* (2013.01); *C01B 2203/0822* (2013.01); *C01B 2203/0877* (2013.01); *C01B 2203/0894* (2013.01); *C01B 2203/1241* (2013.01); *F28D 2021/0022* (2013.01); *C10J 2300/0906* (2013.01); *C10J 2300/0909* (2013.01); *C10J 2300/0916* (2013.01); *C10J 2300/0976* (2013.01); *C10J 2300/0989* (2013.01); *C10J 2300/1223* (2013.01); *C10J 2300/1246* (2013.01); *C10J 2300/1269* (2013.01); *C10J 2300/1292* (2013.01); *C10J 2300/1621* (2013.01); *C10J 2300/1665* (2013.01); *C10J 2300/1687* (2013.01); *C10J 2300/1693* (2013.01); *C10J 2300/1884* (2013.01); *C10J 2300/1892* (2013.01); *C10J 2200/152* (2013.01); *Y02E 50/18* (2013.01); *C10G 2300/1011* (2013.01); *C10G 2400/02* (2013.01); *C10G 2300/807* (2013.01)

(56) References Cited

U.S. PATENT DOCUMENTS

| | | | |
|---|---|---|---|
| 7,553,476 | B2 | 6/2009 | Marrella et al. |
| 7,632,476 | B2 | 12/2009 | Shah et al. |
| 7,686,856 | B2 | 3/2010 | Hemmings et al. |
| 7,856,829 | B2 | 12/2010 | Shah et al. |
| 7,871,457 | B2 | 1/2011 | Shah et al. |
| 7,881,825 | B2 | 2/2011 | Esposito et al. |
| 7,931,888 | B2 | 4/2011 | Drnevich et al. |
| 7,985,399 | B2 | 7/2011 | Drnevich et al. |
| 8,007,761 | B2 | 8/2011 | Drnevich et al. |
| 8,378,151 | B2 | 2/2013 | Perkins et al. |
| 8,814,961 | B2 | 8/2014 | Perkins et al. |
| 2003/0182861 | A1 | 10/2003 | Weimer et al. |
| 2004/0219079 | A1 | 11/2004 | Hagen et al. |
| 2005/0142049 | A1 | 6/2005 | Amsden et al. |
| 2007/0098602 | A1 | 5/2007 | Haueter et al. |
| 2008/0025884 | A1 | 1/2008 | Tonkovich et al. |
| 2008/0039674 | A1 | 2/2008 | Bradley |
| 2008/0086946 | A1* | 4/2008 | Weimer et al. ............ 48/89 |
| 2008/0222955 | A1 | 9/2008 | Jancker et al. |
| 2009/0013601 | A1 | 1/2009 | Mandich et al. |
| 2010/0137459 | A1 | 6/2010 | Stites et al. |
| 2010/0237291 | A1 | 9/2010 | Simmons |
| 2010/0242352 | A1 | 9/2010 | Perkins et al. |
| 2010/0242353 | A1 | 9/2010 | Jovanovic |
| 2010/0242354 | A1 | 9/2010 | Perkins et al. |
| 2010/0243961 | A1 | 9/2010 | Hilton et al. |
| 2010/0247387 | A1 | 9/2010 | Perkins et al. |
| 2010/0249251 | A1 | 9/2010 | Hilton et al. |
| 2010/0249468 | A1 | 9/2010 | Perkins et al. |
| 2010/0270505 | A1 | 10/2010 | Gallaspy et al. |
| 2010/0273899 | A1 | 10/2010 | Winter |
| 2010/0303692 | A1 | 12/2010 | Perkins et al. |
| 2011/0107661 | A1 | 5/2011 | Tirmizi et al. |
| 2011/0124927 | A1 | 5/2011 | Stites et al. |
| 2011/0155958 | A1 | 6/2011 | Winter et al. |
| 2011/0301732 | A1 | 12/2011 | Gao et al. |
| 2012/0181483 | A1 | 7/2012 | Perkins et al. |
| 2012/0241677 | A1 | 9/2012 | Perkins |

OTHER PUBLICATIONS

Bridgwater, et al., "Fast Pyrolysis Processes for Biomass" Renewable and Sustainable Energy Reviews, vol. 4, No. 1, pp. 1-73, Mar. 2000.

Lede, "Solar Thermochemical Conversion of Biomass", Solar Energy, vol. 65, No. 1, 11 pages, Jan. 1, 1999.

Office Action for Chinese Patent Application No. 201080025216.3 mailed Jun. 20, 2013. 5 pages. State Intellectual Property Office of PRC.

Non-Final Office Action for U.S. Appl. No. 12/795,947 mailed Mar. 14, 2013, 28 pages. U.S. Patent and Trademark Office, Alexandria, Virginia USA.

Notification of Transmittal of the International Search Report and the Written Opinion of the International Searching Authority for International Application No. PCT/US2010/037940 mailed Aug. 13, 2010, 11 pages. International Searching Authority/US, Alexandria, Virginia USA.

Notification Concerning Transmittal of International Preliminary Report on Patentability for International Application No. PCT/US2010/037940 mailed Dec. 12, 2011, 10 pages. International Bureau of WIPO, Geneva, Switzerland.

Notification of Transmittal of the International Search Report and the Written Opinion of the International Searching Authority for International Application No. PCT/US2010/059564 mailed Mar. 2, 2011 11 pages. International Searching Authority/US, Alexandria, Virginia USA.

*Netscape Communications Corp. v. ValueClick, Inc.*, 684 F. Supp. 2d. 678—Dist. Court, ED Virginia 2010. No. 1:09cv225. United States District Court, E.D. Virginia, Alexandria Division. Oct. 22, 2009. 38 pages.

*Ex Parte* Wada and Murphy, U.S. Patent and Trademark Office Board of Patent Appeals and Interferences Decision on Appeal dated Jan. 14, 2008, 9 pages.

*Ex Parte* Chapman, U.S. Patent and Trademark Office Board of Patent Appeals and Interferences Decision on Appeal dated Feb. 9, 2012 for Appeal No. 2009-010238, U.S. Appl. No. 10/751,616, 6 pages.

Non-Final Office Action for U.S. Appl. No. 12/795,947 mailed Sep 15, 2014, 31 pages.

Non-Final Office Action for U.S. Appl. No. 12/795,947 mailed Jun. 3, 2014, 30 pages.

Advisory Action for U.S. Appl. No. 12/795,947 mailed Jan. 21, 2014, 4 pages

Final Office Action for U.S. Appl. No. 12/795,947 mailed Oct. 2, 2013, 26 pages.

Examination Report for Australian Patent Application No. 2010355257 mailed Feb. 10, 2015, 4 pages. IP Australia.

First Office Action for Chinese Patent Application No. 201080067327.0 mailed Aug. 5, 2014, 15 pages. State Intellectual Property Office of PRC.

Notice of Allowance for U.S. Appl. No. 13/429,749 mailed Apr. 15, 2014, 18 pages.

Non-Final Office Action for U.S. Appl. No. 13/429,749 mailed Dec. 27, 2013, 14 pages.

* cited by examiner

VARIOUS METHODS AND APPARATUSES FOR AN ULTRA-HIGH HEAT FLUX CHEMICAL REACTOR

RELATED APPLICATIONS

This application is a U.S. national stage application under 35 USC §371 of International Application No. PCT/US2010/059564, filed Dec. 8, 2010, which claims the benefit of both U.S. patent application Ser. No. 12/795,947, filed Jun. 8, 2010 and entitled "SYSTEMS AND METHODS FOR AN INDIRECT RADIATION DRIVEN GASIFIER REACTOR & RECEIVER CONFIGURATION and 2) U.S. Provisional Patent Application Ser. No. 61/380,116, filed Sep. 3, 2010 and entitled "HIGH HEAT FLUX CHEMICAL REACTOR. This application also claims priority under 35 USC 119 to U.S. Provisional Patent Application Ser. No. 61/380,116, filed Sep. 3, 2010 and entitled "HIGH HEAT FLUX CHEMICAL REACTOR. This application also is a continuation-in-part of and claim priority to U.S. patent application Ser. No. 12/795,947, filed Jun. 8, 2010 and entitled "SYSTEMS AND METHODS FOR AN INDIRECT RADIATION DRIVEN GASIFIER REACTOR & RECEIVER CONFIGURATION," which claims the benefit of both U.S. Provisional Patent Application Ser. No. 61/248,282, filed Oct. 2, 2009 and entitled "Various Methods and Apparatuses for Sun Driven Processes," and U.S. Provisional Patent Application Ser. No. 61/185,492, titled "VARIOUS METHODS AND APPARATUSES FOR SOLAR-THERMAL GASIFICATION OF BIOMASS TO PRODUCE SYNTHESIS GAS" filed Jun. 9, 2009.

BACKGROUND

An ultra-high heat flux chemical reactor can be used to drive a number a processes including a process to generate syngas.

SUMMARY

An ultra-high heat flux chemical reactor can be used to drive a number a processes including a process to generate syngas. In an embodiment, the multiple reactor tubes of the ultra-high heat flux chemical reactor are located inside a receiver vessel. A cavity made of highly reflective material distributes radiant energy. The reactor tubes are configured to pass 1) methane 2) natural gas, 3) steam 4) biomass particles and 5) any combination of the four through a heat transfer aid to cause a steam methane reaction and a gasification of the biomass particles to occur at the same time using the thermal energy from the radiant energy.

The heat transfer aid is used to heat the reactant gases. The heat transfer aid is one or more of the following located inside each reactor tube: a fluidized bed or entrained flow of biomass particles, a fluidized bed or entrained flow of chemically inert particles, reticulate porous ceramic (RPC) foam, a ceramic monolith, ceramic tubes or aerogels, open structured packed rings including Raschig rings, gauze or wire constructed of a high temperature-resistant material, and any combination of these. Radiation is the primary mode of heat transfer to the heat transfer aids and chemical reactants from the reactor tube walls, and conduction, convection, or some combination of the two are the secondary modes of heat transfer from the cavity walls and reactor tubes.

A length and diameter dimensions of the gasification reaction zone of each of the reactor tubes is sized to give the very short residence time of 0.01 second to 5 second at the gasification temperatures of at least 900 degrees C. The reaction products have a temperature from the exit of the gasification zone that equals or exceeds 900 degrees C. The multiple reactor tubes in this chemical reactor design increase available reactor surface area for radiative exchange to the biomass particles, as well as inter-tube radiation exchange. The source of the radiant heat maybe one or more of solar energy, gas-fired regenerative burners, nuclear power, and electric heaters, and any combination of these.

BRIEF DESCRIPTION OF THE DRAWINGS

The multiple drawings refer to the example embodiments of the invention.

Figure 1:
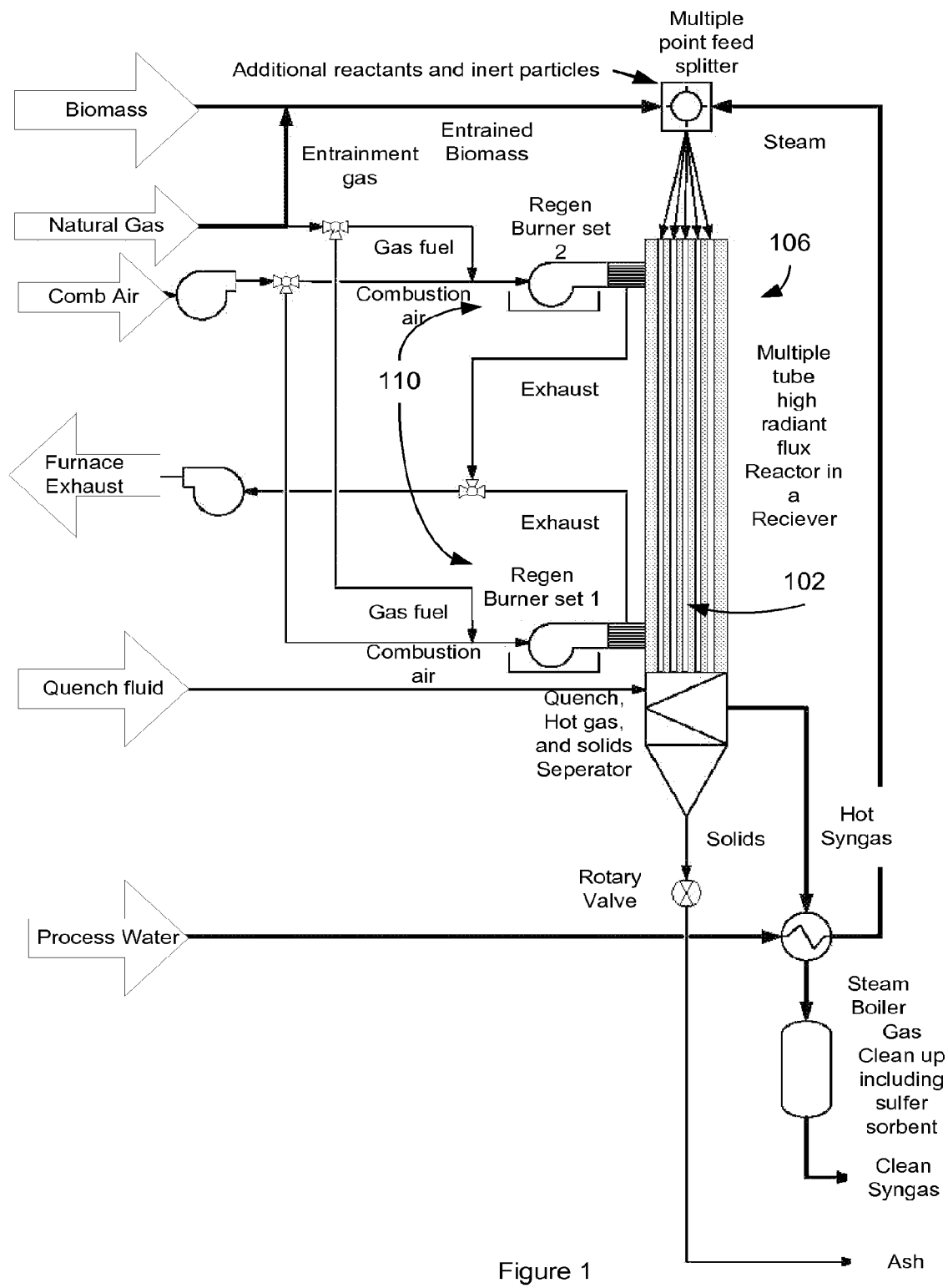
FIG. 1 illustrates a flow schematic of an embodiment for the high-flux chemical reactor implemented for biomass gasification using regenerative natural gas burners as a heat source.

While the invention is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the invention.

DETAILED DISCUSSION

In the following description, numerous specific details are set forth, such as examples of specific chemicals, named components, connections, types of heat sources, etc., in order to provide a thorough understanding of the present invention. It will be apparent, however, to one skilled in the art that the present invention may be practiced without these specific details. In other instances, well known components or methods have not been described in detail but rather in a block diagram in order to avoid unnecessarily obscuring the present invention. Thus, the specific details set forth are merely exemplary. The specific details may be varied from and still be contemplated to be within the spirit and scope of the present invention.

A number of example processes for and apparatuses associated with an ultra-high heat flux chemical reactor and its associated integrated chemical plant are described. The following drawings and text describe various example implementations of the design. Thus, several example high radiant heat flux chemical reactor are described that generate chemical products, and several example chemical reactions are also discussed. For example, the source of the radiant heat may be one or more of 1) solar energy, 2) gas-fired regenerative burners, 3) nuclear power, 4) electric heaters and 5) any combination of these four. For example, the endothermic chemical reaction conducted in the reactor tubes includes one or more of the following: biomass gasification, steam methane reforming, methane cracking, a dry reforming reaction, steam methane cracking to produce ethylene, metals refining, and CO2 or H2O splitting and various combinations of these reactions, to be conducted in this chemical reactor using primarily the radiant heat energy. This design encompasses an ultra-high heat flux chemical reactor to generate chemical products, for example, synthesis gas products. One skilled in the art will understand parts and aspects of many of the designs discussed below within this illustrative document may be used as stand-alone concepts or in combination with each other.

FIG. 1 illustrates a flow schematic of an embodiment for the high-flux chemical reactor implemented for biomass gasification using regenerative natural gas burners as a heat source.

The high heat flux driven chemical reactor 102 has a downdraft geometry with the multiple reactor tubes in a vertical orientation located inside the cavity of the thermal receiver 106. A chemical reaction driven by radiant heat occurs within the multiple reactor tubes. The cavity is made of highly reflective material that distributes radiant energy and, the receiver 106 encloses multiple reactor tubes of the ultra-high heat flux chemical reactor 102. The reactor tubes are configured to pass multiple chemical reactants including 1) methane 2) natural gas, 3) steam 4) biomass particles and 5) any combination of the four, through the tubes to cause a steam methane reaction and a gasification of the biomass particles using the thermal energy from the radiant energy.

The ultra-high heat flux/high temperature entrained flow chemical reactor 102 is driven primarily by radiative heat transfer, and not convection or conduction. Thus, radiative heat transfer drives the high heat flux. Typical gas chemical reactors use convection or conduction to transfer energy, and these have effective heat transfer coefficients between 20 W/m^2 and 100 W/m^2, giving effective heat transfer fluxes below 10 kW/m^2 (for up to a 100° C. driving temperature difference). Using radiation at high temperature (>1000 degrees C. wall temperature), much higher fluxes can be achieved (100-250 kW/m^2). For heat transfer limited reactions, the size of capital equipment is reduced linearly with the flux, and capital cost is greatly reduced. Typical chemical reactors, all driven by convection and/or conduction, simply cannot achieve these flux rates or size of process equipment.

The gas-fired regenerative burners 110 supply heat energy to the chemical reactor 102. The inside wall of the receiver 106 absorbs or highly reflects the concentrated energy from the regenerative burners 110 positioned along the walls of the receiver 106 cavity to cause energy transport by thermal radiation and reflection to generally convey that heat flux to the biomass particles inside the walls of the reactor tubes. The receiver 106 inner wall absorbs or highly reflects the regenerative burners 110 to cause a radiant heat and then generally radiatively transmits that heat to the biomass particles in the tubes of the solar driven chemical reactor 102. An inner wall of the receiver 106 cavity may be made of material to allow the receiver 106 cavity to be operated at high, >1200 degrees C., wall temperatures to enable the high heat transfer rates, rapid reaction kinetics of the very short residence time, and high selectivity of carbon monoxide and hydrogen produced from the gasification reaction for syngas.

In an embodiment, particles of biomass are gasified in the presence of a steam (H2O) carrier gas and methane (CH4) in a simultaneous steam reformation and steam biomass gasification reaction to produce reaction products that include hydrogen and carbon monoxide gas using the ultra-high heat flux thermal energy radiated from the inner wall and then into the multiple reactor tubes. The steam reacts with both the biomass and the methane, but biomass and methane does not react with each other. A steam (H2O) to carbon molar ratio is in the range of 1:1 to 1:4, and the temperature is high enough that the chemical reaction occurs without the presence of a catalyst.

One or more heat transfer aids may be used to heat the chemical reactant gases. The heat transfer aid may be one or more of the following (flowing particulates and/or structured packing) located inside each reactor tube: a fluidized bed or entrained flow of biomass particles, a fluidized bed or entrained flow of chemically inert particles, reticulate porous ceramic (RPC) foam, a ceramic monolith, ceramic tubes or aerogels, open structured packed rings including Raschig rings, gauze or wire constructed of a high temperature-resistant material, and any combination of these. These heat radiation absorbing materials act as heat transfer aids that can be used in the reactor tubes to increase heat transfer to reactant gases and other materials (operating at 20-50 times the heat flux of conventional gas phase chemical reactors). Radiation is the primary mode of heat transfer to the heat transfer aids from the reactor tube walls, and conduction, convection, or some combination of the two are the secondary modes of heat transfer from the cavity walls and reactor tubes.

Rather than using a complex configuration (microchannels, very small diameter tubes, etc) for increasing convective surface area, the reactor can use a very large tube and allow the large surface area to volume ratio of the particles flowing within the tubes to improve convection heat transfer to gas phase reactants. The particles act as direct absorbers, effectively increasing the emissivity of the particle-laden gas stream. Radiation heat transfer increases with the fourth power of temperature, so the absorbing particles can absorb very high flux from the wall with a very small temperature differential. Their high surface area then allows effective transfer to the gas with a low temperature differential between gas and particulates. A structured packing with a very open structure (so that heat transfer within the structure is driven primarily by radiation) works in a similar manner. With this method, the reactors can be simple large tubes, with low manufacturing cost, well understood fluid dynamics, and simpler scaling relations than the convection optimized structures for competitive chemical reactors.

In some embodiments, the high temperatures of the chemical reactor 102 can be used to heat particles entrained in the gas flow to sufficient temperatures to chemically change the particles. For example, if the particles are coated with a metal ferrite compound, the high-flux reactor can be use to change the oxidation state of the metal ferrite coating.

After the reaction in the chemical reactor occurs, then rapid cooling occurs to capture the reaction products. A quench zone is located immediately downstream of an exit of the chemical reactor 102 to immediately quench via rapid cooling of at least the hydrogen and carbon monoxide of the reaction products of exiting the chemical reactor 102. This achieves within 10 seconds a temperature after quenching of 800 degrees C. or less, which is below a level to reduce coalescence of ash remnants of the biomass particles. The cooling generally occurs to preferably equal to or less than 400 degrees C. within the 10 seconds of exiting the chemical reactor 102. At the exit of the gasification reaction zone in the reactor tubes of the chemical reactor 102, two or more of the multiple reactor tubes form into a group at the exit and that group combines their reaction products and un-reacted particles from the biomass gasification into a larger pipe per group that forms a portion of the quench zone. One or more sprayers inside the larger pipe inject a cooling fluid directly into the reaction product syngas stream to make the temperature transition from the at least 900 degree C. exit temperature to less than the 400 degrees C. within the 0.1-10 seconds to prevent metal dusting corrosion of the pipe walls.

A sulfur removal sorbent, present in either the biomass gasification process or initially introduced in the quench zone, reduces an amount of sulfur present in a syngas stream exiting the quench zone. One or more hot particle filters to remove particulates from the syngas stream exiting the quench zone, where the particulates are sent to an ash holding vessel. The products from the chemical reaction are supplied to a downstream chemical synthesis plant.

Note, the reactor tubes serve the dual functions of 1) segregating the biomass gasification reaction environment from the atmosphere of the receiver cavity and 2) transferring energy by radiation absorption and heat radiation, convection, and conduction to the reacting particles of biomass to drive the endothermic gasification reaction of the particles of biomass flowing through the reactor tubes. The high heat transfer rates of the reactor tubes and cavity walls allow the particles of biomass to achieve a high enough temperature necessary for substantial tar destruction and gasification of greater than 90 percent of the biomass particles into reaction products including the hydrogen and carbon monoxide gas in a very short residence time between a range of 0.01 and 5 seconds.

Each set of regenerative burners 110 may work as follows. Regeneration uses a pair of burners 110, which cycle to alternately heat the combustion air or recover and store the heat from the furnace exhaust gases. When one regenerative burner is firing, the other is exhausting the furnace gases. Exhaust gases pass through the regenerative burner body and into a media case, which contains refractory material. The refractory media is heated by the exhaust gases, thus recovering and storing energy from the flue products. When the media bed is fully heated, the regenerative burner currently firing is turned off and begins to exhaust the flue products. The regenerative burner with the hot media bed begins firing. Combustion air passes through the media bed and is heated by the hot refractory. Air preheat temperatures within 300 degrees F.-500 degrees F. of the furnace temperature are achieved resulting in exceptionally high thermal efficiency.

A high temperature is achieved and maintained for these temperature-favored equilibrium reactions. The design of the chemical reactor 102 drives chemistry to desired products at these temperatures. Thus, in the case of endothermic reactions, this yields a higher conversion rate into products from the chemical reaction (and in an example case resulting in higher quality syngas). This includes biomass gasification (elimination of tars, and the secondary reformation reactions of by-product CH4 to CO and H2), steam methane reforming, ethylene production by steam ethane reforming, methane cracking for carbon black and hydrogen formation, and other high temperature chemical reactions.

The ultra-high heat fluxes driven by the high operating temperatures can be suitable for driving a variety of commercially desirable reactions including: Biomass gasification; Coal gasification; Steam methane reforming; Dry methane reforming; Ethylene pyrolysis, ethylene dichloride cracking (pyrolysis); Naphtha cracking, ethane cracking; Carbon black production via methane cracking; Hydrogen production via metal ferrite redox cycles; and other similar reactions.

Note, biomass gasification is an endothermic process. Energy must be put into the process to drive it forward. Typically, this is performed by partially oxidizing (burning) the biomass itself. Between 30% and 40% of the biomass must be consumed to drive the process, and at the temperatures which the process is generally limited to (for efficiency reasons), conversion is typically limited, giving still lower yields. A typical theoretical gasoline yield for a standard gasification process is 50 gallons of gasoline/ton of biomass. The ultra-high heat flux chemical reactor 102 process uses an external source of energy (such as concentrated solar energy) to provide the energy required for reaction, so none of the biomass need be consumed to achieve the conversion. This results in significantly higher yields (100 gallons of gasoline per ton). As the energy source being used to drive the conversion is renewable and carbon free, (in the case of concentrated solar energy) it is eligible for carbon credits and/or will not be adversely affected by carbon penalties in the future.

Competing reactors for these reactions are not able to operate at these high temperatures because they have a combination of the following two:

Catalysts—catalytic systems are typically used for kinetically limited reactions, and must remain below certain temperatures to avoid sintering of the catalytic sites which would reduce the yields and productivity of the reactor. This design allows chemical reactions without the use of a catalyst.

Materials—materials of reactor construction are not high temperature compatible or do not have the high thermal conductivity required to pass heat to the chemical reaction effectively. The configuration of these reactors is typically complex to improve contact area for heat transfer/catalysis, which does not lend itself to being manufactured out of the high temperature ceramic materials used for this implementation.

Thus, the high reactor temperatures allow certain chemical reaction, such as steam methane reforming (SMR), to occur at high throughput and without the aid of a catalyst, resulting in lower production costs over low-temperature systems that require use of an expensive catalyst that must be periodically replaced.

Figure 2:
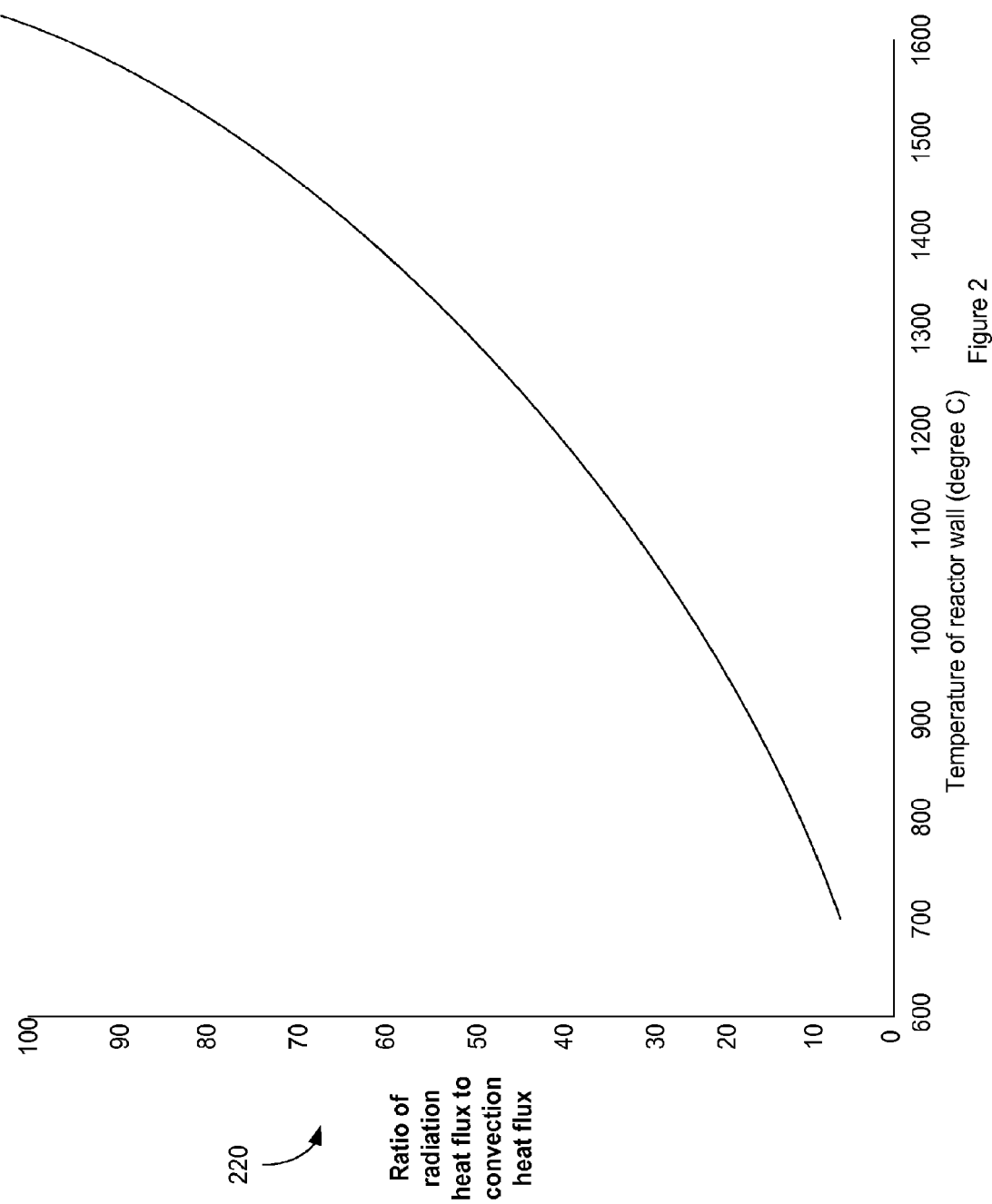
FIG. 2 illustrates a chart of a ratio of radiation heat flux to convection heat flux at various temperatures for an embodiment of the receiver—reactor design, illustrating that radiation is the dominant heat transfer mechanisms at the high operating temperatures of the high-flux chemical reactor.

FIG. 2 illustrates a chart of a ratio of radiation heat flux to convection heat flux at various temperatures for an embodiment of the receiver—reactor design, illustrating that radiation is the dominant heat transfer mechanisms at the high operating temperatures of the high-flux chemical reactor. The chart 220 shows at a reactor tube temperature of around 700 degrees, then the ratio of radiation heat flux to convection heat flux is around 7 to 1. As the reactor tube temperature increases to around 1400 degrees, then the ratio of radiation heat flux to convection heat flux is around 60 to 1. As the reactor tube temperature increases to around 1600 degrees, then the ratio of radiation heat flux to convection heat flux is around 100 to 1. The ratio of radiation heat flux to conduction heat flux is similarly quite discrepant at these high temperatures in this receiver—reactor design.

Generally, the operational temperature of the high heat flux driven chemical reactor is maintained at greater than 900 degrees C. and up above 1100 degrees C in most cases. The values of heat flux at these operating temperatures are high in this design. For example, a high heat flux of 100-250 kW/m^2 is achieved by radiative heat transfer through the selected material of the reactor tube walls at a high temperature of equal to or greater than 1000 degrees C. wall temperature.

The entrained-flow of chemical reactants into the chemical reactor may start when the ultra-high heat flux chemical reactor is at least a minimum operational temperature of 750 degrees Celsius and preferably greater than 1000 degrees Celsius. The chemical reactor converts carbonaceous biomass materials into carbon monoxide and hydrogen by reacting the raw particles of biomass material with the steam for biomass gasification, and the steam with the supplemental methane for steam reforming at high temperatures, 700-1600 degrees C., with a controlled amount of steam, natural gas, and any combination, which then results in the gas mixture of synthesis gas.

The ability to operate at elevated reactor tube temperatures in combination with gas-phase heat transfer aids drives endothermic, heat transfer limited (as opposed to kinetically limited), chemical reactions to occur at shorter residence times and with a significant (20-50 times) reduction in the required area of heat transfer surface, resulting in higher conversion rates and reduced formation of undesirable byproducts (such as tars in the case of incomplete biomass gasification), producing a higher quality and quantity of product gas (e.g. syngas in the case of biomass gasification). The design gives a large throughput due to high operating temperatures, shorter residence times, and multiple reactor tubes. The design increases conversion efficiency at the same or less residence time within the reactor due to the combination of high heat flux and higher reaction temperatures, thus increasing overall plant conversion efficiencies & yields at lower equipment capital costs. The design reduces required surface area of reactor tubes by 20-50 times, thus reducing the materials cost for reactor tubes & manifolds (SiC or super-alloys). The design reduces production of unwanted secondary byproducts (e.g. tar in biomass gasification). Thus the design reduces cost & complexity of gas cleanup systems prior to subsequent unit operations; and reduces cost, complexity and handling/disposal requirements for inert solid byproducts (e.g. ash) as a potential contamination of a saleable byproduct or as a waste disposal problem because no tar was produced to contaminate the ash. An additional advantage of the reduced required surface area is that corrosion of key components can be slowed because corrosion rates are surface area specific.

As discussed, the ultra-high heat flux chemical reactor is driven by the high flux and high temperature that the materials and accordingly the multiple tubes design of the reactor and the wall of the cavity are built to withstand and achieve this high flux and high temperature. High flux gives lower capital cost, decreasing production cost for end products (e.g. gasoline) and improving return on investment. The higher temperature enables better per pass conversion of chemical reactions to occur without catalysis, improving productivity for a given capital investment and reducing overall operating costs (less recycle/wasted feedstock). Additionally, high temperature allows operation in regimes where unwanted byproducts (e.g. tar in biomass gasification) are not produced, reducing the necessary capital investment and operational costs of additional processing steps.

Also, the energy source for driving the endothermic chemical reaction comes from the source of the radiant heat, rather than by burning the biomass itself, and where the multiple reactor tubes and cavity walls of the receiver and transfer energy primarily by radiation absorption and re-radiation, rather than by convection or conduction, to the reactants in the chemical reaction to drive the endothermic chemical reaction flowing in the reactor tubes.

Figure 3:
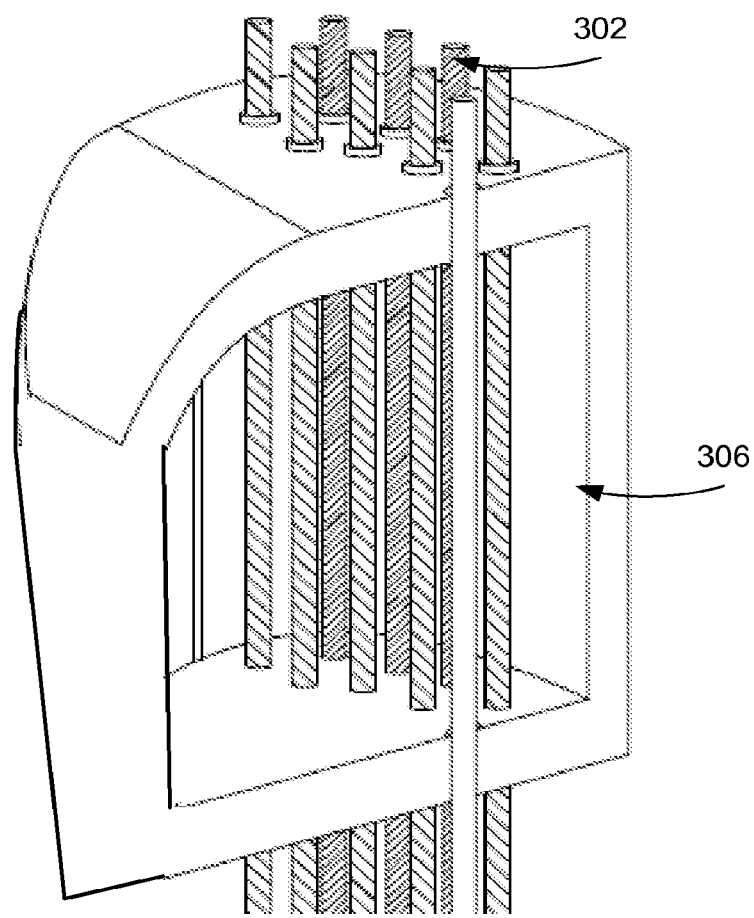
FIG. 3 illustrates a cut away view of an embodiment for the receiver cavity enclosing offset and staggered reactor tubes.

FIG. 3 illustrates a cut away view of an embodiment for the receiver cavity enclosing offset and staggered reactor tubes. The thermal receiver 306 has a cavity with an inner wall. The radiation driven geometry of the cavity wall of the thermal receiver 306 relative to the reactor tubes 302 locates the multiple tubes 302 of the chemical reactor as offset and in a staggered arrangement inside the receiver 306. A surface area of the cavity walls is greater than an area occupied by the reactor tubes 302 to allow radiation to reach areas on the tubes 302 from multiple angles. The inner wall of the receiver 306 cavity and the reactor tubes 302 exchange energy primarily by radiation, with the walls and tubes 302 acting as re-emitters of radiation to achieve a high radiative heat flux reaching all of the tubes 302, and thus, avoid shielding and blocking the radiation from reaching the tubes 302, allowing for the reactor tubes 302 to achieve a fairly uniform temperature profile from the start to the end of the reaction zone in the reactor tubes 302.

Thus, the geometry of the reactor tubes 302 and cavity wall shapes a distribution of incident radiation with these 1) staggered and offset tubes 302 that are combined with 2) a large diameter cavity wall compared to an area occupied by the enclosed tubes 302, and additionally 3) combined with an inter-tube radiation exchange between the multiple reactor tube geometric arrangement relative to each other where the geometry. The wall is made of material that highly reflects radiation or absorbs and re-emits the radiation. The shaping of the distribution of the incident radiation uses both reflection and absorption of radiation within the cavity of the receiver 306. Accordingly, the inner wall of the thermal receiver 306 is aligned to and acts as a radiation distributor by either 1) absorbing and re-emitting radiant energy, 2) highly reflecting the incident radiation to the tubes 302, or 3) any combination of these, to maintain an operational temperature of the enclosed ultra-high heat flux chemical reactor. The radiation from the 1) cavity walls, 2) directly from the regenerative burners, and 3) from an outside wall of other tubes acting as re-emitters of radiation is absorbed by the reactor tubes 302, and then the heat is transferred by conduction to the inner wall of the reactor tubes 302 where the heat radiates to the reacting particles and gases at temperatures between 900 degrees C. and 1600 degrees C., and preferably above 1100 degrees C.

As discussed, the inner wall of the cavity of the receiver 306 and the reactor tubes 302 exchange energy between each other primarily by radiation, not by convection or conduction, allowing for the reactor tubes 302 to achieve a fairly uniform temperature profile even though generally lower temperature biomass particles and entrainment gas enter the reactor tubes 302 in the reaction zone from a first entrance point and traverse through the heated cavity to exit the reaction zone at a second exit point. This radiation heat transfer from the inner wall and the reactor tubes 302 drives the chemical reaction and causes the temperature of the chemical reactants to rapidly rise to close to the temperature of the products and other effluent materials departing from the exit of the reactor.

A length and diameter dimensions of a gasification reaction zone of each of the reactor tubes 302 is sized to give the very short residence time of 0.01 second to 5 second at the gasification temperatures of at least 900 degrees C., and an exit of the gasification zone in the multiple reactor tubes 302. The reaction products have a temperature from the exit of the gasification zone that equals or exceeds 900 degrees C., and the multiple reactor tubes 302 in this chemical reactor design increase available reactor surface area for radiative exchange to the biomass particles, as well as inter-tube radiation exchange. A rapid gasification of dispersed falling biomass particulates with a resultant stable ash formation occurs within a residence time within the reaction zone in the reactor tubes 302 in the less than 5 seconds, resulting in a complete amelioration of tar to less than 500 milligrams per normal cubic meter, and at least a 90% conversion of the biomass into the production of the hydrogen and carbon monoxide products.

The design reduces the required surface area of the reactor tubes 302 and furnace interior, thus reducing the size, weight, and cost of the furnace chamber (size & weight are important for tower-mounted solar applications as well as other applications).

To achieve high conversion and selectivity, biomass gasification requires temperatures in excess of 1000° C. These are difficult to achieve in standard fluidized bed gasifiers, because higher temperatures requires combustion of an ever larger portion of the biomass itself. As a result, indirect and fluidized bed gasification is typically limited to temperatures of 800° C. At these temperatures, production of unwanted higher hydrocarbons (tars) is significant. These tars clog up downstream equipment and foul/deactivate catalyst surfaces, requiring significant capital investment (10-30% of total plant cost) in tar removal equipment. High heat flux thermal systems are able to achieve high temperatures very efficiently. More importantly, the efficiency of the process can be controlled as a function of concentration and desired temperature, and is no longer linked to the fraction of biomass lost to achieving high temperature. As a result, temperatures in the tar cracking regime (1000-1300° C.) can be achieved without any loss of fuel yield from the biomass or overall process efficiency. This removes the complex train of tar cracking equipment typically associated with a biomass gasification system. Additionally, operation at high temperatures improves heat transfer and decreases required residence time, decreasing the size of the chemical reactor and its capital cost.

The temperatures of operation, clearly delineated with wall temperatures between 1200° C. and 1450° C. and exit gas temperatures in excess of 900° C. but not above silica melting temperatures (1600° C.) is not typically seen in gasification, and certainly not seen in indirect (circulating fluidized bed) gasification. The potential to do co-gasification of biomass and steam reforming of natural gas which can be done in the ultra-high heat flux chemical reactor could not be done in a partial oxidation gasifier (as the methane would preferentially burn). The process' feedstock flexibility derives from the simple tubular design, and most gasifiers, for reasons discussed herein, cannot handle a diverse range of fuels.

A material making up the inner wall of the receiver 306 cavity has mechanical and chemical properties to retain its structural strength at high temperatures between 1100-1600° C., have very high emissivity of $\epsilon > 0.8$ or high reflectivity of $\epsilon < 0.2$, as well as high heat capacity (>200 J/kg-K), and low thermal conductivity (<1 W/m-K) for the receiver 306 cavity. A material making up the reactor tubes 302 possesses high emissivity ($\epsilon > 0.8$), high thermal conductivity (>1 W/m-K), moderate to high heat capacity (>150 J/kg-K).

Figure 4:
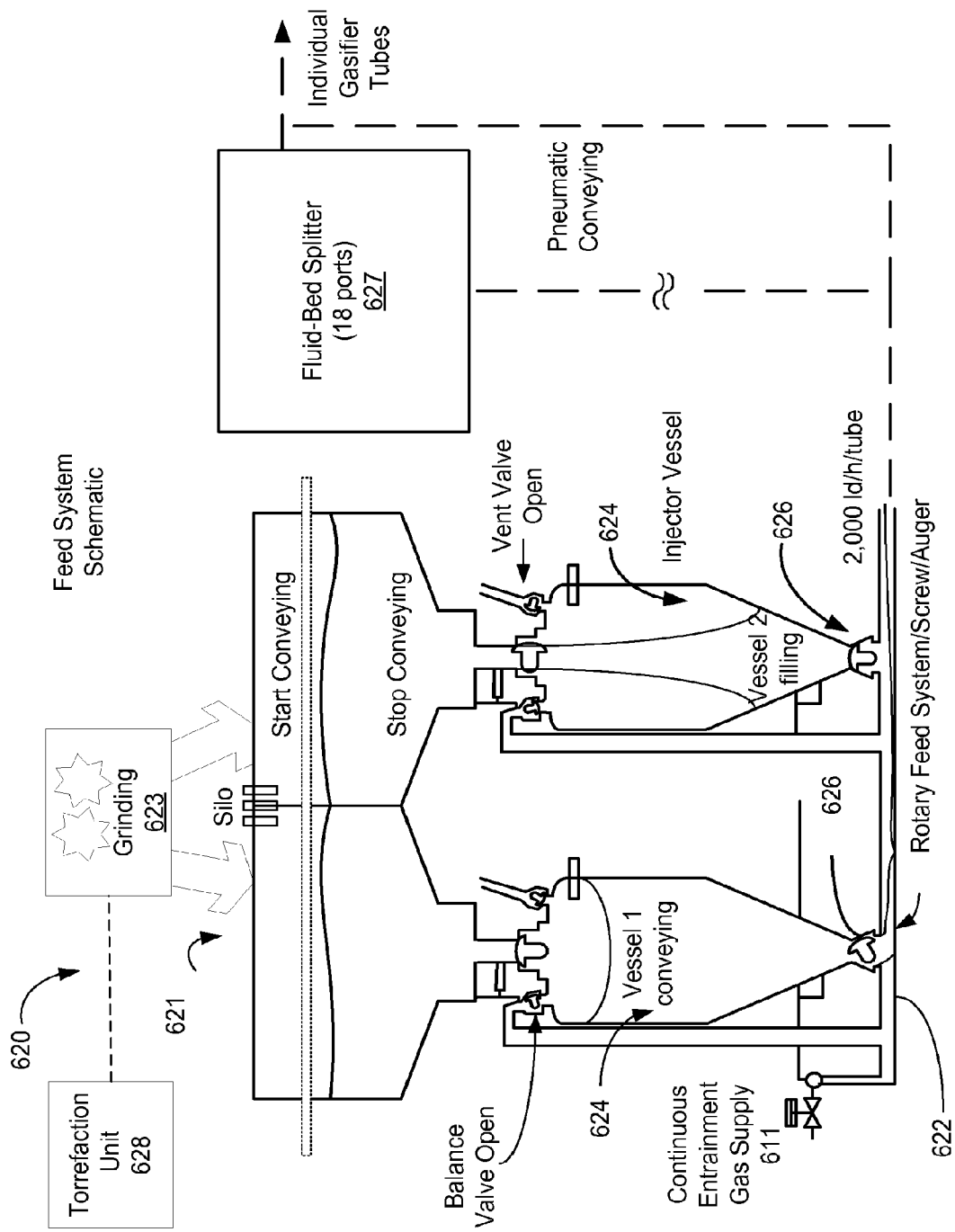
FIGS. 4 and 5 illustrate embodiments for an entrained-flow biomass feed system that supplies the biomass particles in a carrier gas to the chemical reactor.
Figure 5:
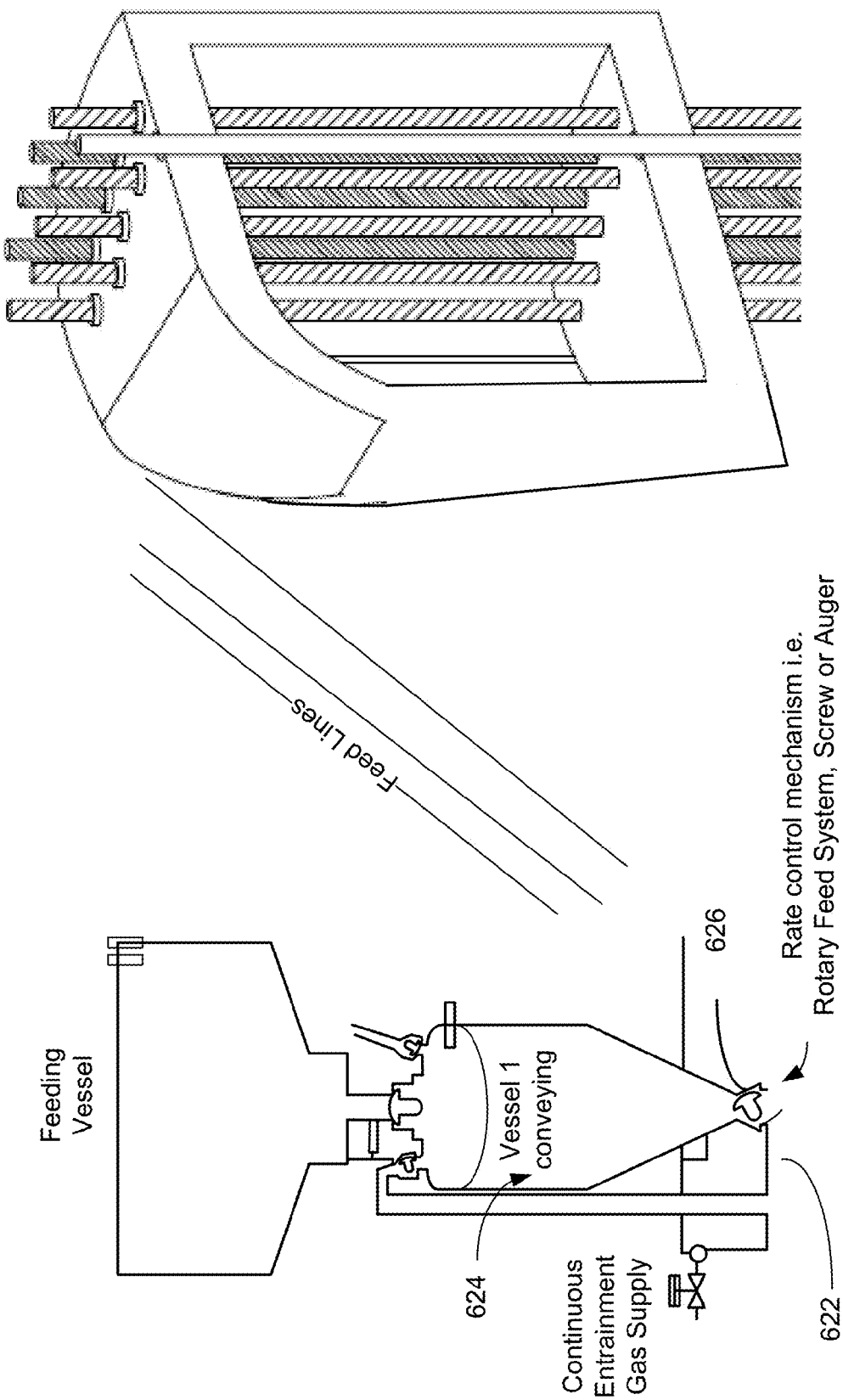

FIGS. 4 and 5 illustrate embodiments for an entrained-flow biomass feed system that supplies the biomass particles in a carrier gas to the chemical reactor.

The entrained-flow biomass feed system 620 can include a pressurized lock hopper pair 624 that feeds the biomass to a rotating metering feed screw 622 and then into an entrainment gas pipe at the exit 626 of the lock hopper pair. The particles of the biomass are distributed into multiple entrainment gas lines by a flow splitter 627 to feed the two or more reactor tubes making up the chemical reactor.

In an embodiment, the high heat flux reactor and associated integrated system may also include the entrained-flow biomass feed system 620 having one or more lock-hopper pairs 624 equipped with a single multi-outlet feed splitter 627 that simultaneously feeds the particles of the biomass in pressurized entrainment gas lines into two or more tubes of the chemical reactor. The tubes may be controlled as discrete tube sets, each with two or more tubes. The gas source 611 may also supply pressurized entrainment gas in the form of recycled carbon dioxide from an amine acid gas removal step in the hydrocarbon fuel synthesis process, steam, or some other carrier gas. The multi-outlet feed splitter 627 provides and controls an amount of distribution of the particles of the biomass in the one or more pressurized entrainment gas lines that feed the two or more reactor tubes in the chemical reactor via allowing flow or no flow through a set of reactor tubes. Thus, each feeding vessel 624 of the biomass feed system supplies a feed splitter 627 that feeds, for example up to twelve reactor tubes in the chemical reactor. Each feeding vessel 624 has one or more outlets 626 configured to supply a consistent volumetric amount of biomass particles within ten percent of the demand signal amount when distributing biomass particles to the two or more reactor tubes.

The high heat flux reactor and associated integrated system may also include a grinding system 623. The grinding system 623 has a grinding device that is at least one of 1) a mechanical cutting device, 2) a shearing device, 3) a pulverizing device, and 4) any combination of these that breaks apart the biomass, and a series perforated filters in the entrained-flow biomass feed system. The grinding device and perforated filters grind the partially pyrolyzed biomass from the torrefaction unit 628 to control the particle size of the biomass to be between 50 um and 1000 um. The entrained-flow biomass feed system is feedstock flexible to be able to supply multiple different types of biomass without changing the feed or reactor process via at least particle size control of the biomass and that the energy source for the chemical reaction comes from an external source, rather than burning the biomass itself. The torrefaction unit 628 is geographically located on the same site as the ultra-high heat flux chemical reactor and configured to be subject the biomass to partial pyrolysis with recouped waste heat from the chemical reaction in a temperature range of up to 300 degrees C. to make the biomass 1) brittle and easier for grinding, 2) dryer, less sticky, and easier to feed in a conveying system, 3) subject to less spoilage issues in storage as a torrefied biomass, as well as 4) produce off gases from the torrefaction process. The torrefaction unit 628 supplies partially pyrolyzed biomass to the grinding system 623. The torrefaction of the partially pyrolyzed biomass reduces the energy required by the grinding device to grind the biomass to the controlled particle size between 50 um and 1000 um. The off gases from the torrefaction of the biomass can be used for one or more of the 1) entrainment carrier gas, 2) an energy source for steam generation, or 3) a gas for the gas-fired regenerative burners.

The feedstock flexibility of being able to use multiple types of biomass without redesigning the feed and reactor process clearly gives an economic advantage over processes that are limited to one or a few available feed stocks. By heating the reactor tubes with radiant energy (which re-radiate to the particles), the problem of generating heat for the reaction and designing the reactor to conduct the reaction (essentially the endothermic/exothermic balancing problem) is eliminated.

A flow enhancer, including a bulkmatology flow enhancer or a porous-walled tube, may also be used in the feed system to control an amount of entrainment carrier gas carrying the particles of biomass entering a gasification reaction zone of the reactor tubes by reducing velocity of the carrier gas just prior to an entrance to a gasification reaction zone of the reactor tubes by removing a controlled portion of the carrier gas through the flow enhancer in response to a feedback signal.

Figure 6:
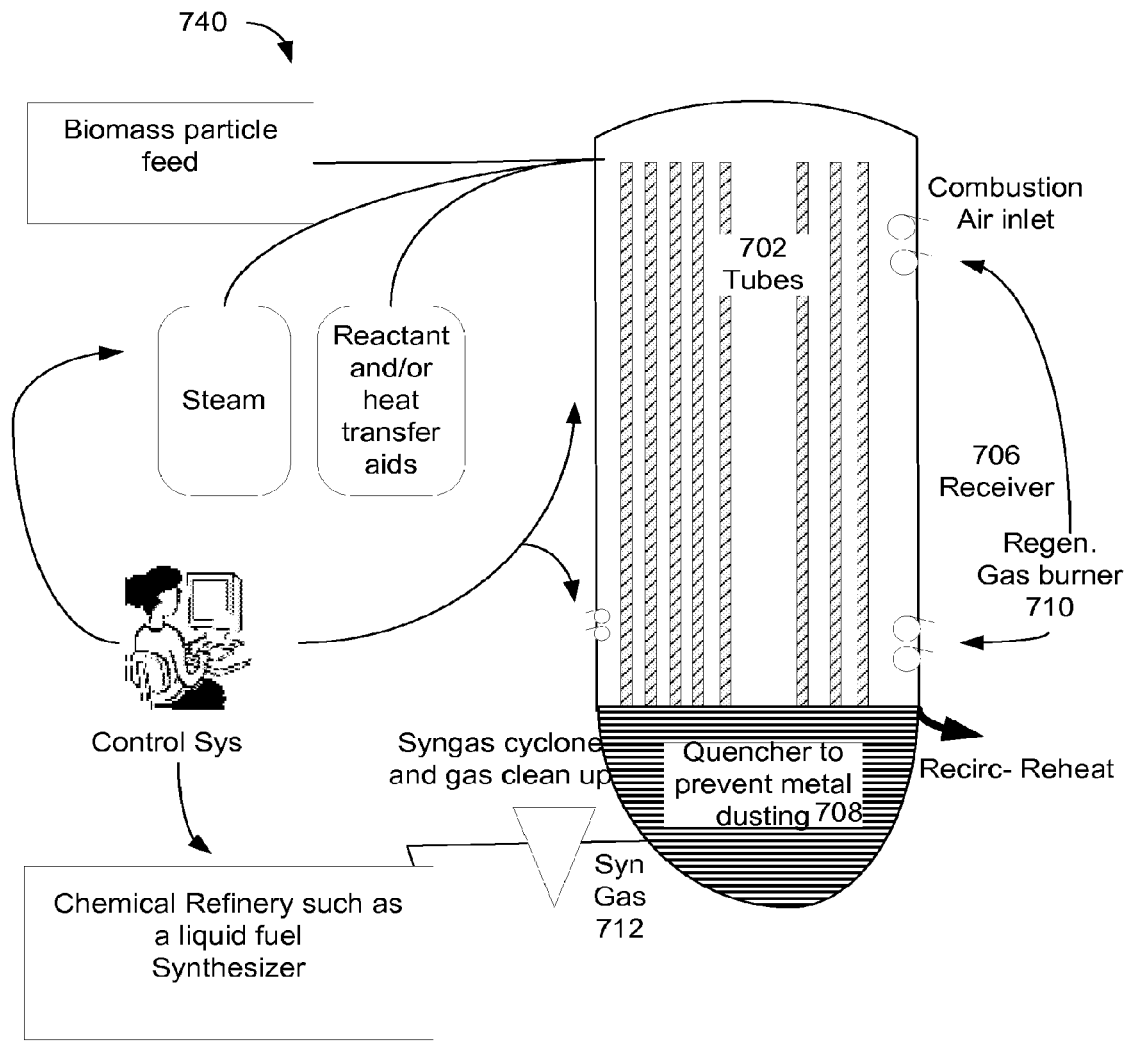
FIG. 6 illustrates a diagram of an embodiment of a high heat flux driven bio-refinery with multiple control systems that interact with each other.

FIG. 6 illustrates a diagram of an embodiment of a high heat flux driven bio-refinery with multiple control systems that interact with each other. In such a system, radiant heat energy may be provided to the reactor 702. The chemical reactor/furnace of the ultra-high heat flux chemical reactor can be heated by a variety of means to ensure 24/7 operations (either singularly or in combination) including: Concentrated solar energy; Electrical resistive heating; Electrical induction heating; Direct or indirect gas (or other conventional fuel) burner heating; Nuclear reactor (direct, or by collection of waste heat); Steam heating, as part of a waste-heat recovery system; Boilers, as part of a waste-heat recovery system. In an embodiment, steam can be delivered at the temperatures necessary to drive the external convective/radiant fluxes sufficient for the internal radiant flux rates required; and, other similar radiant heat sources. In this example, the chemical reactor may be heated by two or more sets of the gas-fired regenerative burners 710.

An entrainment carrier gas system supplies carrier gas for the particles of biomass in the feed system to the chemical reactor. The other chemical reactants and/or steam may also be delivered to the reactor tubes. As illustrated, chemical reactants, including biomass particles, may flow into the chemical reactor 702 and syngas flows out 712. The quench unit 708 may be used to rapidly cool the reaction products and prevent a back reaction into larger molecules.

The computerized control system may be multiple control systems that interact with each other. The computerized control system is configured to send a feed demand signal to feed system's to control an amount of 1) reactor tube sets to be fed particles of biomass in the chemical reactor, 2) amount of gas fired regenerative burners supplying heat, 3) rate at which particular gas fired regenerative burners supply heat, and 4) any combination of these based on control signals and the temperature measured for the chemical reactor. The control system may rely on feedback parameters including temperature of the reactor as well as feed forward parameters including anticipated changes in heat in from the burners and heat out from changes in an amount of chemical reactants and carrier gas being passed through the reactor tubes 702. The control system for the integrated plant sends control signals to and receives feedback from a control system for the ultra-high heat flux chemical reactor. The control system for the ultra-high heat flux chemical reactor at least indicates the amount of product being generated in the ultra-high heat flux chemical reactor, the temperature, the amount of heats currently active, and other similar parameters. The control system may balance chemical reaction types, including a biomass gasification reaction, a stream reforming reaction, a dry reforming reaction and various combinations of these reactions within the chemical reactor to maintain the generated syngas within the desired molar ratio of H2 to CO ratio of 2.1:1 to 2.8:1 with being substantially tar free having less than 200 mg/m^3 of tar, and having less than 15% by volume CO2 in the generated syngas. In general, the high heat transfer rates of the reactor tubes and cavity walls maintained by the control system allow the particles of biomass to achieve a high enough temperature necessary for substantial tar destruction and gasification of greater than 90 percent of the biomass particles into reaction products including the hydrogen and carbon monoxide gas in a very short residence time between a range of 0.01 and 5 seconds.

The control system may control the multiple reactor tubes via splitting operation of them into two or more groups of tube subsets. The control system can do both for the integrated plant 1) control the feed to match the amount of energy, as well as control the radiant energy to match the amount of feed, now that system has the ability to control the amount of energy/heat sink out via increase or decrease amount of carrier gas and reactant flowing in a given set of reactor tubes as well as control heat into the reactor by 1) controlling an amount of fuel gas flowing in a given set of regenerative burners, 2) starting up additional sets of regenerative burners inside the thermal receiver, or any combination of these.

The control systems of the reactor and liquid fuel plant may have bi-directional communications between the chemical reactor and the liquid fuel plant, such as a methanol plant. For example, when a subset of tubes needs to be adjusted out for maintenance or due to a failure, then the integrated plant can continue to operate with increase biomass and entrainment gas flow through the chemical reactor to keep a steady production of syngas for conversion into a liquid fuel. Changing entrainment gas pressure in the reactor tubes can also be used to increase/decrease the heat sink effect of the biomass and gas passing through the tubes.

The integrated chemical plant converts the supplied chemical reactants, such as particles of biomass, into gasoline in the integrated chemical plant as follows. The hydrogen and carbon monoxide products from the chemical reactor are converted in an on-site methanol synthesis plant to methanol, and the methanol from the methanol synthesis plant is converted to gasoline in a methanol-to-gas process. The on-site chemical synthesis reactor, such as a methanol synthesis plant, is geographically located on the same site as the chemical reactor and integrated to receive the hydrogen and carbon monoxide products in the form of syngas. The on-site chemical synthesis reactor has an input to receive the syngas, which contains the hydrogen and carbon monoxide products from the chemical reactor, and then is configured to use the syngas in a hydrocarbon synthesis process to create a liquid hydrocarbon fuel or other chemical. The methanol production from syngas production is decoupled from being directly tied the momentary rate of syngas production by storing excess syngas, supplying supplemental syngas, or idling methanol reactors.

A moving bed of carbonaceous feedstock may be in the reactor through which the gasification agent flows in a co-current or counter-current configuration to achieve gasification and the bed is heated with thermal energy.

The multiple reactor tubes making up the high heat flux chemical reactor can be made of a material, including SiC or coated graphite, that retains structural integrity at temperatures greater than 950 degrees C. and as high as 1600 degrees C. Due to these high operating temperatures in the reactor, radiation is now the primary mode of heat transfer between the (furnace/receiver) cavity walls and the reactor tubes. There is also significant inter-tube and intra-tube heat transfer via radiation and re-absorption, resulting in a high degree of circumferential and axial uniformity in the temperature of the reactor tubes; thereby, this uniform temperature profile allows chemical reactions to occur consistently throughout the entire volume of the tubes. The temperature profile along the reactor tube is substantially constant but the heat flux is subject to large gradients compared to the temperature variation.

The reactor tubes are materially made of refractory ceramics or metals, where the material chosen must have good chemical stability and high strength at high temperatures between 1100-1600 degrees C., high corrosion and abrasion resistance rates for the particle size of the biomass and steam concentration, high oxidation resistance at high temperatures if the receiver cavity is filled with a non-inert gas including air, good at absorbing solar energy, high re-radiating properties via radiation emissivity ($\epsilon > 0.8$), and high thermal conductivity (>1 W/m-K). The material chosen for tube construction may be selected from the example group of materials, individually or in combination, including silicon-carbide, silicon-carbide coated graphite, Tungsten, molybdenum, mullite, zirconia, molybdenum with Aluminum Sulfide, Sintered submicron silicon carbide powder, transparent sapphire, high aluminum content nickel-base alloys, and refractory ceramics including aluminum oxide (Al2O3).

An additional advantage of a high-flux reactor using an external energy source is that any carbon dioxide produced by the external energy source (a natural gas burner, for example) is isolated from the product gases produced in the reactor tubes. For example, in conventional gasifiers in which 30-40% of the biomass is oxidized to drive the gasification process, the resulting carbon dioxide is contained in the product syngas, requiring further purification of the syngas and thus added costs.

Also, a dry reform of the methane with CO2 either contained within the natural gas or fed as a separate feedstock occurs in the chemical reactor, such that, even if some CO2 is present in the natural gas consisting mainly of methane, the CO2 and CH4 react with the high heat via dry reforming to produce hydrogen and carbon monoxide.

1. Various important reactor or furnace design concepts that allow for efficient operation at the high temperatures necessary for ultra-high heat fluxes include as follows.

The design of the reactor has multiple reactor tubes. A receiver or furnace encloses the reactor tubes, rather than a sealed and pressurized vessel enclosing each tube as in the case of a fluid-wall reactor.

The design of the reactor is capable of using biomass as a feedstock to produce syngas.

The design may have multiple unique chemical reactions occurring at the same time within the chemical reactor, either within the same tube or within different tube sets that pass there chemical reactants through the receiver cavity at the same time.

The design of the reactor has the orientation of energy flow through the reactor tubes from the outside to inside because they are heated from the outside (rather than by a reaction inside, like in some variants of biomass gasification). The design of the reactor has very high temperatures at the outer wall and energy conducts through the tube to re-radiate on the other side.

The material of reactor construction may use a high temperature monolithic single phase ceramic as the material of construction. In contrast, nearly all gasification and gas reforming chemical reactors are constructed of metal or refractory-lined metal. The design of the reactor may have multiple ceramic (e.g. SiC) heat transfer/reactor tubes in a single cavity reactor furnace.

Configuration: The reactor tube is simple tube or other shape of an internal diameter of at least 3.5" in a blackbody cavity. Competitive chemical reactors try to give more surface area for convective transfer.

The reactor tubes are non-porous (and thus not operated in a fluid wall configuration), because the high operating temperatures don't require a fluid wall to keep the interior of the reactor tubes clean.

Recovery and re-use of waste heat from high temperature flue gases in the case of 1) the gas-fired regenerative burners reactor, recuperative combustion air pre-heaters, torrefaction unit, waste heat boilers for steam, and other processes heated by the flue gases.

The design of the reactor has refractory materials possibly with the use of high emissivity coatings that line the outer wall of a furnace or solar receiver. These linings reflect as well as absorb and re-emit radiant energy from the original energy source (which may be concentrated solar energy or fuel-fired burners) and insulates the furnace cavity to reduce energy losses.

Doors/shutters/air curtains when implementing a solar/non-solar hybrid operation.

The ultra-high heat flux chemical reactor uses heat transfer media. The process uses an absorbing particle or a structured packing to absorb radiation and transfer it convectively to the gas from the reactor wall. Absorbing particles can include the reactant itself, as in the case of biomass gasification, or inert particles, such as a proppant. Structured packings include, for example, reticulated porous ceramic (RPC) forms. Conventional reactors simply use convection from the reactor wall alone without the additional absorbing particle also assisting in this heat transfer process.

The use of inert particles as a heat transfer aid can be implemented in an entrained-low configuration, where the particles flow co-currently with the reactants, for example. In another example, the inert particles can be implemented in a fluidized bed configuration.

The ultra-high heat flux chemical reactor uses high flux radiation as the primary method of heat transfer (as described above).

The ultra-high heat flux chemical reactor conducts operation at wall temperatures in excess of 1200° C., allowing rapid conversion, higher equilibrium conversion, and destruction of unwanted side products.

The ultra-high heat flux chemical reactor has a downward, gravity/entrainment gas-driven flow of particles and gas in a simple multiple tubular reactor design.

The ultra-high heat flux chemical reactor may use a receiver/furnace with an indirect radiation-driven design, where the energy radiates from the refractory material on the inside walls of the furnace and the reactor tubes themselves, rather than the heat source itself.

The ultra-high heat flux chemical reactor may use non-porous reactor tubes that allow the use of gas burners (possibly with regenerative waste heat recovery or recuperative combustion air pre-heaters) with flue gases inside the furnace, because the reactant and product materials/gases inside the reactor tubes are isolated from the environment inside the furnace.

The ultra-high heat flux chemical reactor may have syngas production as the produced product via a biomass gasification reaction inside the reactor. The biomass gasification reaction may occur with other reactions in the reactor.

The ultra-high heat flux chemical reactor may have hydrogen production via metal ferrite redox cycles.

The ultra-high heat flux chemical reactor may have a reactor furnace including one or multiple heat sources for high intensity radiant heat transfer. The heat sources may include floor or wall mounted fuel-fired burners within a refractory-lined furnace, concentrated solar thermal energy entering into a refractory-lined furnace through an aperture in a side wall, Ultra-high temperature burners, direct-fired regenerative or radiant impingement wall type burners, burning commercial fuels (e.g. natural gas) or downstream reactor waste/byproduct gases or liquids as a fuel, utilizing preheated combustion air with or without oxygen enrichment, firing within an insulated furnace operating at refractory wall temperatures up to 1600° C. that results in indirect radiant heat transfer to gas/aerosol reactants contained within multiple ceramic reactor tubes operating at wall temperatures up to 1600° C.

Reactor furnace operating at 20-50 times increase in heat transfer rates compared to conventional high temperature process furnaces 1) for heat transfer limited (not kinetically limited) endothermic reactors with high radiant heat transfer into gas/aerosol entrained flow reactants flowing within impermeable solid tubes operating at higher wall temperatures (up to 1400° C.) than conventional alloy based reactor tubes.

The ultra high heat flux chemical reactor can be made of a material to support high heat flux driven by radiative heat transfer to a falling reactant particle or open structured package within the reactor walls/tubes. The generated heat flux at the reactor tube wall interface may be 10 or greater times (such as 100-250 kW/m2) than that in typical chemical reactors. High operating temperatures allow radiation to be the primary energy driver driving the chemical reaction rather than conductive or convective heating.

Note, a chemical reactor is the container in which a chemical reaction occurs. The chemical reactor may be a single reactor tube, or a set of reactor tubes. Thus, the chemical reactor may be a single reactor with multiple reactor tubes or multiple reactors each being a single reactor tube, or some other similar combination. Further, different chemical reactions may take place in different reactor tubes of the high heat flux chemical reactor. For example, Steam Methane Reforming may occur in a first set of reactor tubes and biomass gasification may occur in another set of reactor tubes making up the chemical reactor, which is at least partially contained in the thermal receiver. Likewise, different chemical reactions may take place in the same reactor tubes of the chemical reactor at the same time. Also, the control system may control the chemical reactions occurring within the reactor tubes via a number of mechanisms. For example, the flow rate of the chemical reactants, such as biomass particles and carrier gas, into and through the reactor tubes is controlled, along with a concentration of each reactant flowing through the reactor tube. The control system may control each reactor tube individually, or in sets/groups of for example clusters of eighteen tubes, or all of the tubes in their entirety.

The shape, orientation, and other features of the reactor tubes may vary. A first of the multiple tubes may have a different diameter than a second of the multiple tubes. For example, tubes exposed to higher radiation fluxes may be smaller in diameter, and tubes exposed to lower radiation fluxes may be larger in diameter, thereby delivering the same particle heating rates with variable radiation fluxes. Additionally, the shape of each tube might be a cylindrical shaped pipe, a rectangular shaped pipe, or some other shaped pipe.

In an embodiment, the amount of reactor tubes present in the cavity of the thermal receiver may be in a preferred range of 120-150 reactor tubes, with a range encompassing as few as 30 reactor tubes and as many as multiple hundreds. Each reactor tube will have the same size diameter the rest of the reactor tubes. The geometric arrangement of the multiple reactor tubes relative to each other may be an arc pattern or some other geometric arrangement with possibly more than one row. The length and diameter dimensions of the gasification reaction zone in the reactor tubes is the inner diameter of the tubes will be 3.5 inches and stretch the full length of the tube such as 7 meters long.

In the chemical reactor with multiple reactor tubes, a separate entrainment line may be used for each of the gasifier reactor tubes in the chemical reactor. As discussed, this may allow for independent temperature control and balancing of amount of chemical reactant(s) and inert heat-transfer particles flowing in each of the reactor tubes. When the chemical reactants are biomass, the particles of biomass feed can be distributed to the reactor tubes by a lock hopper rotary feed system, such as a lock hopper rotary feed system. Such a system can allow for balanced feeding to individual reactor tubes and feed rate of the particles is controlled in a number of ways.

The indirect simple tubular reactor design is not only less difficult to design, but less likely to fail during operation.

Figure 7:
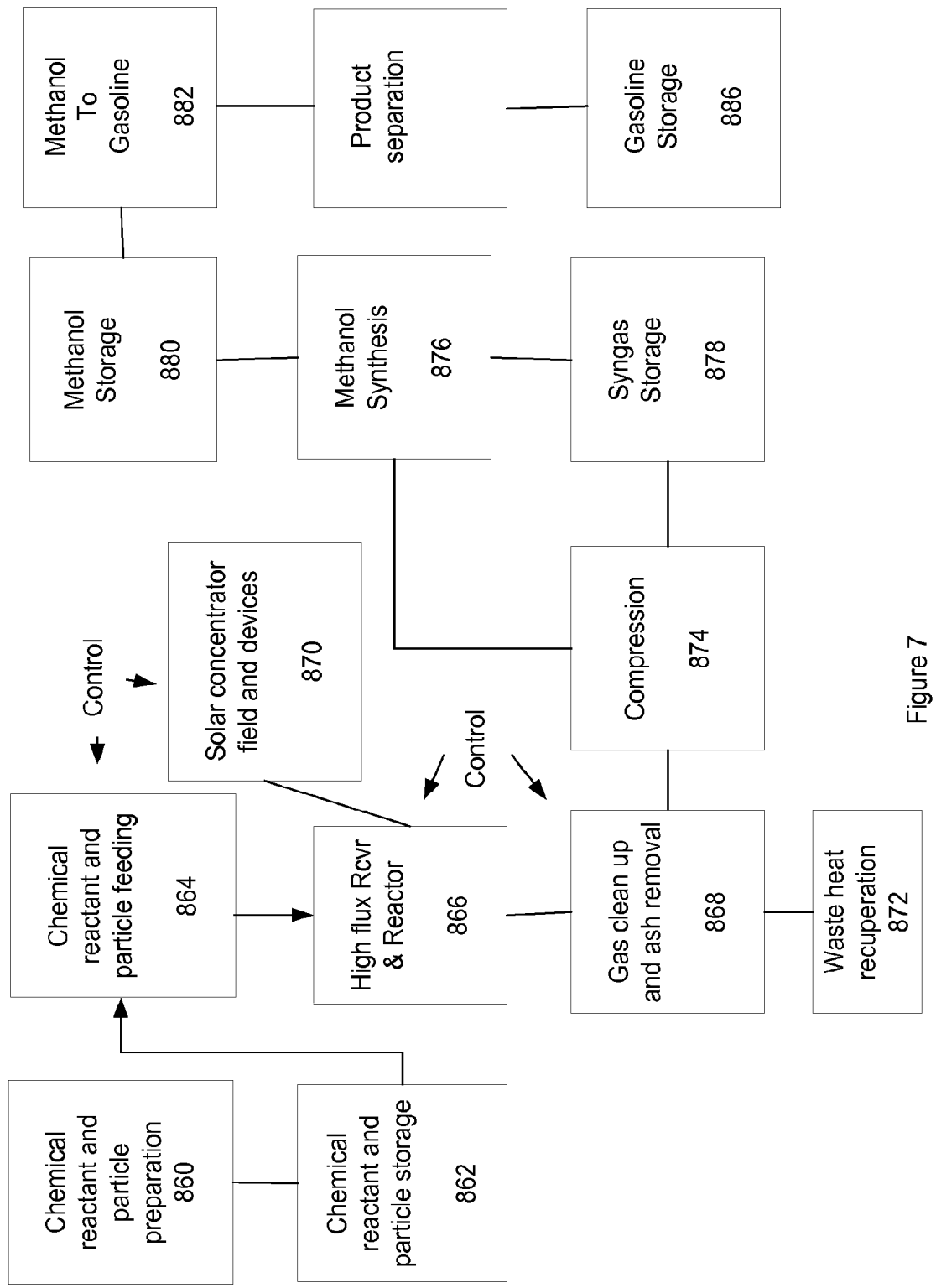
FIG. 7 illustrates a block diagram of an embodiment of an example integrated process flow for the reactor and its associated plant.

FIG. 7 illustrates a block diagram of an embodiment of an example integrated process flow for the reactor and its associated plant. In an embodiment, the integrated process with the ultra-high heat flux chemical reactor has several major process steps: including the following.

Chemical reactant(s) preparation occurs with subsequent feeding into the ultra-high heat flux chemical reactor. For example, this may include biomass grinding or densification, transport and offload 860, storage 862, and feeding 864.

Equipment generally used for grinding biomass includes impact mills (e.g. hammer mills), attrition mills, and kinetic disintegration mills-KDS (e.g. flail mills). A hammer mill system, KDS, or similar system can be used to grind the bales (loaded by conveyer) into particles, which are to be fed into the radiant heat flux thermal gasifier. The ground particles have an average screen size between 500 microns (um) and 1000 um in diameter, and are loaded into, a silo with a standard belt conveyer or with a positive or negative pressure pneumatic conveying system. The ground particles may also have an average screen size between 50 microns (um) and 1000 um, 50 microns (um) and 200 um, 50 microns (um) and 2000 um and various combinations.

The various chemical reactants and inert particles for the reaction including biomass may then be stored 862 on site. As needed, the chemical reactants and inert particles will be fed 864 into an example radiant heat flux-driven chemical reactor via a feed system. For example, after grinding and pulverizing the biomass to particles, a lock-hopper feed system feeds the particles of biomass into the radiant heat flux-driven chemical reactor to be gasified. The feed system can supply the variety and types of biomass. The radiant heat flux receiver and gasifier 866 may be used to thermally decompose the biomass.

In a solar embodiment, various heliostat field designs and operations drive the biomass gasifier. Some example designs may include a solar concentrator, secondary concentrator, focused mirror array, etc. to drive biomass gasifier 870.

Quenching, gas clean up, and ash removal from biomass gasifier 868 may be provided for. Some non-pilot syngas may exit the system 872. Some gasses may be a waste product, while other gasses can be compressed 874 prior to storage 878 or e.g., methanol synthesis 876. Methanol may then be stored 880 for later methanol to gasoline conversion 882.

In various embodiments, synthesis gas may be feed to another technical application. Examples include a syngas to other chemical conversion process. The other chemical of chemicals produced can include liquefied fuels such as transportation liquefied fuels. Some transportation liquefied fuels include jet fuel, DME, gasoline, diesel, and mixed alcohol, bio-char with a high sequestered amount of carbon; chemical production, electricity generation, synthetic natural gas production, heating oil generation, and other similar syngas based technical applications. In an example hydrocarbon based fuel, e.g., methanol, 876 may be formed from syngas. The methanol may be further converted to gasoline or other fuels 882 and various products may be separated out from the gasoline 884 or syngas. These products, e.g., gasoline, may then be stored for later use as an energy source.

If an intermediate chemical was produced from the ultra-high heat flux chemical reactor, that resultant product may be fed to other processes in the integrated plant. For example, a synthesis gas may be fed to a technical application. These technical applications include syngas to a transportation liquefied fuels such as jet fuel, DME, gasoline, diesel, methanol, and mixed alcohol, bio-char with a high sequestered amount of carbon; chemical production, electricity generation, synthetic natural gas production; heating oil generation; and other similar syngas based technical applications.

Figure 8:
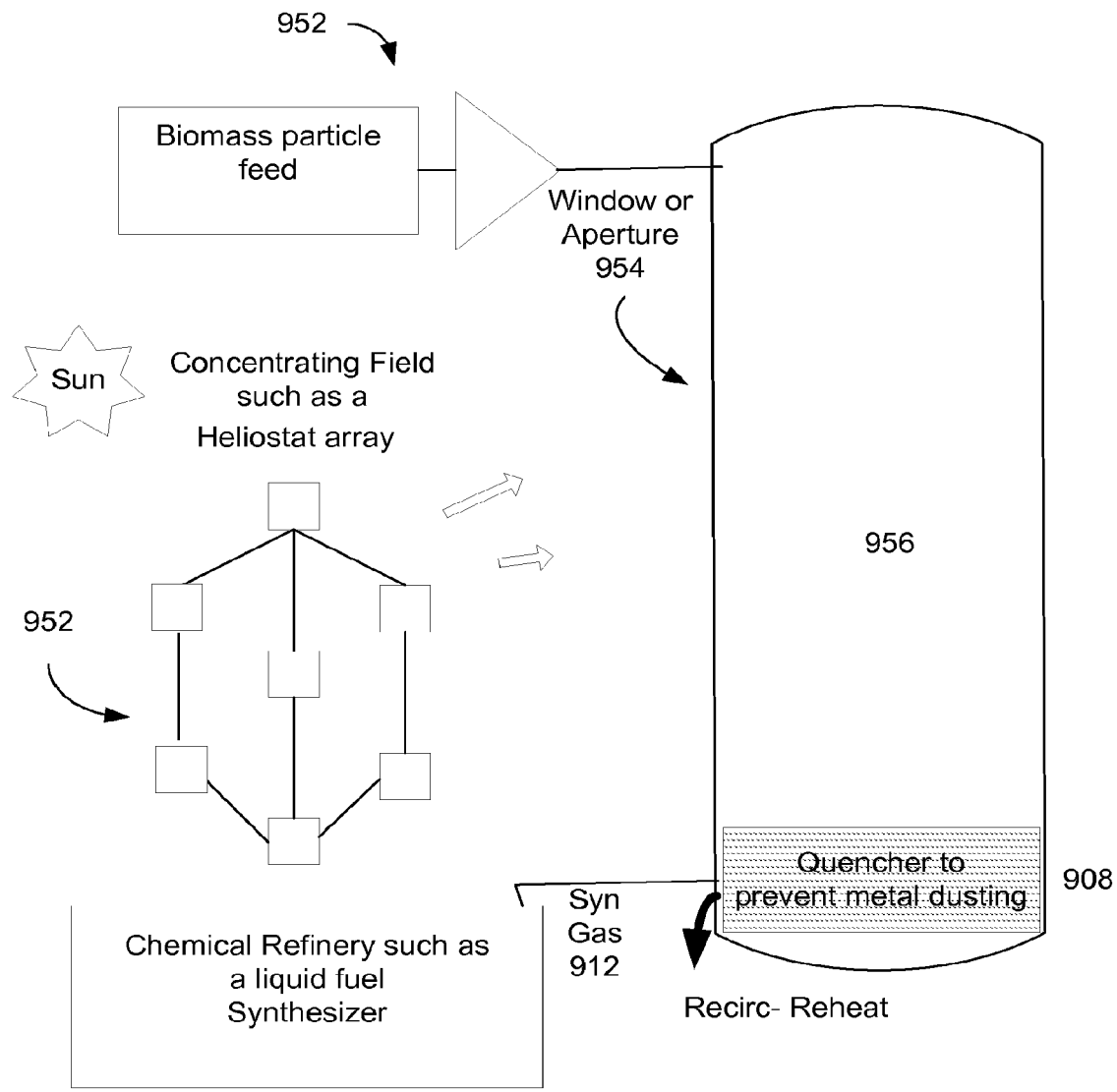
FIG. 8 illustrates a diagram of an embodiment of a solar-driven bio-refinery.

FIG. 8 illustrates a diagram of an embodiment of a solar-driven bio-refinery. In such a system, solar power 952 may be provided through a window or aperture 954 to a solar heated receiver and reactor 956. A quencher 908 may be used to prevent back reaction. As illustrated, chemical reactants including biomass particles, steam and other chemicals as well as inert particles may flow into the system and syngas flows out 912.

The high-flux reactor can efficiently use concentrated solar energy, which is inherently high flux. The ultra high heat flux chemical reactor is a solar driven chemical reactor and the chemical reactants are biomass particles entrained in a carrier gas. The ultra high heat flux chemical reactor has significant technical advantages. These include:

Simple indirect reactor design that allows for feedstock flexibility and obviates the need for exothermic/endothermic reaction balancing because the energy supplied to drive the reaction is not provided by the partial oxidation of the reactants.

Falling particle design that maximizes heat transfer from reactor walls and removes inherent reactivity limitations.

Absorbing, insulating receiver cavity design to spread solar flux, improve uniformity, and increase overall system efficiency.

Multiple reactor tubes in receiver design to increase available reactor surface area for radiative exchange to particles and intertube radiation exchange.

The receiver's use of an indirect radiation, absorbing cavity receiver with multiple tubular downdraft particle reactors is completely unique to the solar thermal processing world (as well as the biomass gasification world).

Next, a falling particle reactor is an efficient way to get thermal energy into reacting solid particulates (or gases). Heat transfer from the reactor tubes to the reacting and/or non-reacting particles can occur by conduction, convection, or radiation. Even the heated non-reacting particles can be used for many purposes discussed in this document. At moderate temperatures, convection and conduction dominate when transferring energy to a fluid, but these require large amounts of surface area to be effective. As a result, the solar flux on the surface transferring heat must be small, necessarily leading to low temperatures. To get around this problem, radiation heat transfer is required, which requires temperatures above 1000 degrees C. (and preferably above 1200 degrees C.). However, if the surface area being radiated to is small, local temperatures will get high and efficiencies will be low. A dispersed particle reactor solves this problem by greatly increasing the receiving surface area (it is essentially the surface area of the particles). The particles tend to average energy amongst themselves at our volumetric loadings, giving a uniform radial reaction profile. If it is the gas that is desired to be heated (for steam reforming of methane or methane cracking, for example), inert particles can be used as radiation receivers and convection can be used to drive energy from the particles to the gas. Because the surface area of the particles is so large (as compared to the tube surface area), convection heat transfer is no longer a limitation.

Additionally, the use of small particles increases the surface area for reaction. As reactions with gas phase components (e.g. steam, CO2) are surface area specific, the increased surface area greatly increases the reaction rate. Compared to direct view receivers, packed beds, or rotary kilns, reaction rates can be many orders of magnitude higher. As compared to fluidized beds, heat transfer rates are similar, but there is no disengagement of volatile ash components (alkalis) that can deposit downstream and foul critical system components.

In an implementation using concentrated solar energy, the design makes use of a cavity receiver that has a high flux concentration at the aperture as well as multiple (or even single) reactor tubes in the center of the cavity whose inner atmosphere is sealed from the atmosphere of the cavity. This latter point gives separation of the reaction environment (which does not tolerate oxygen) from the cavity environment, allowing the cavity to be open to the atmosphere. This obviates the need for a window (and to keep a window clean) a major cost and size limitation for standard direct view chemical reactor designs (here, "direct view" refers to any receiver where solar energy directly impinges on the chemical reactants). An insulating cavity approach is essentially a blackbody cavity. Conductive losses can be controlled by changing the thickness of the insulation, and convective losses can be controlled through aperture design, orientation, and cavity working fluid (buoyancy). The key advantage of the blackbody cavity is control of the radiative losses, which are entirely determined by the cavity temperature and the average concentration at the aperture. The cavity acts like an oven, spreading heat flux around through radiation and giving a much more even flux profile on the reactor tubes (azimuthally and axially) than the incident solar radiation has. This is a major advantage for a solar field, where the moving sun shifts the beam from west to east weighting across the aperture through the course of each day.

Using solar thermal energy enables very high temperatures (>1000 degrees C.) to be achieved efficiently (i.e. without using up lots of the biomass). At these high temperatures, larger hydrocarbons and aromatic compounds collectively known as tars are broken down into carbon monoxide, hydrogen, and methane. Tar removal is a capitally intensive part of standard biomass gasification plants and adds to operating costs; when essentially no tar is produced, as in the ultra-high heat flux chemical reactor process, these can be avoided.

As stated above, downdraft gasifiers that are indirectly heated are rare for standard gasification. More importantly, the design is not limited to biomass gasification. Multiple chemistries (steam methane reforming, methane cracking, steam ethane cracking to produce ethylene, metals refining, CO2 capture) can be conducted in this reactor using solar thermal energy.

Some modifications occur for the Syngas to Methanol process (as an example generated liquid fuel) when implemented as a solar-driven high heat flux reactor. Adaption to the design with ties between the control system and storage occur for a variable amount of syngas fed into the process. Keeping high pressure syngas storage and parallel trains of methanol reactors that maintain their full reaction temperature and pressure 24-7 occurs even when no syngas is flowing. The control system has algorithms and operational routines established to tolerate transient flow of syngas operation. The ability to perform routine cycling of the chemical reactor and rates of production in the methanol synthesis plant are designed in, due to the diurnal solar energy source. Also, gas feedstock buffers and diurnal solar energy production are added for the solar implementation.

Next, the various algorithms and processes for the control system may be described in the general context of computer-executable instructions, such as program modules, being executed by a computer. Generally, program modules include routines, programs, objects, components, data structures, etc. that perform particular tasks or implement particular abstract data types. Those skilled in the art can implement the description and/or figures herein as computer-executable instructions, which can be embodied on any form of computer readable media discussed below. In general, the program modules may be implemented as software instructions, Logic blocks of electronic hardware, and a combination of both. The software portion may be stored on a machine-readable medium and written in any number of programming languages such as Java, C++, C, etc. The machine readable medium may be a hard drive, external drive, DRAM, Tape Drives, memory sticks, etc. Therefore, the component parts, such as the transaction manager, etc. may be fabricated exclusively of hardware logic, hardware logic interacting with software, or solely software.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. These algorithms may be written in a number of different software programming languages. Also, an algorithm may be implemented with lines of code in software, configured logic gates in software, or a combination of both.

It should be borne in mind, however, that all of these and similar terms are to be associated with the appropriate physical quantities and are merely convenient labels applied to these quantities. Unless specifically stated otherwise as apparent from the above discussions, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers, or other such information storage, transmission or display devices.

Solar collectors including heliostats and/or waste heat from plant processes can be utilized to drive the torrefaction process use on the biomass. Some advantages of using torrefaction on the biomass gasification technology include:

Normalization of biomass feed for the feed system gasification process allows the feed system to utilize a broader array of biomass feedstocks.

Torrefied biomass feedstock suppresses the formation of methane in the biomass gasification process that contaminates syngas product generated from the high flux chemical reactor and adversely affects downstream liquid fuel processing plant.

Torrefied biomass feedstock allows the grinders to more easily obtain finer particles of biomass with a more uniform size distribution, which improves the performance of the high flux chemical reactor gasification process.

Torrefied biomass feedstock allows the volatiles resulting from the torrefaction process to be used as fuel in the gas burner to aid in heat generation for the gasification reaction in the high flux chemical reactor.

Torrefied feedstock allows for:

Removing potential contaminants (volatiles) from the raw feedstock that would otherwise contaminate syngas product from the gasifier and use those to fuel gas burners supplying the heat for SDF gasifier; where tar and chars are generated when the raw biomass is exposed to temperatures above 350 degrees; however, those are now generated in the torrefaction process and the grinder crushes and pulverizes the torrefied biomass into fine particles. When a heat steam carrier gas carries the particles of torrefied biomass the tars and chars are for the most part already removed from that biomass and thus are not present to clog up the feeding tubing; Also, higher temperature dry steam can be used as a carrier gas for the particles of torrefied biomass, which will prevent the moisture in the steam from condensating in the feed system components;

Reducing recycle purges on fuel synthesis, thus improving overall productivity of SDF process; and Reducing ash handling loading and processes for SDF process.

The feed system is able to lower biomass processing operational expenses to improve the cost benefit of its gasification process (OpEx) (lower energy expenditure for reaching target particle size reduction).

The feed system is able to reduce/decrease capital equipment associated with biomass feeding into the SDF gasification process (CapEx) (size of the solids handling equipment due to an increase in bulk density, fewer higher capacity size reduction units).

The feed system is able to improve overall system and gasifier performance via the use of torrefied biomass.

While some specific embodiments of the invention have been shown the invention is not to be limited to these embodiments. For example, the recuperated waste heat from various plant processes can be used to pre-heat combustion air, or can be used for other similar heating means. Regenerative gas burners or conventional burners can be used as a heat source for the furnace. The high flux reactor can be used for any type of endothermic reaction in any aspect of the chemical industry discussed herein. The invention is to be understood as not limited by the specific embodiments described herein, but only by scope of the appended claims.

The invention claimed is:

1. An ultra-high heat flux chemical reactor, comprising:
a thermal receiver having a nontransparent cavity with an inner wall, where the thermal receiver is made of materials and aligned to 1) absorb and re-emit radiant heat energy with an emissivity of greater than 0.8, 2) highly reflect the radiant heat energy with an emissivity of less than 0.2, and 3) any combination of these, to maintain an operational temperature of the enclosed ultra-high heat flux chemical reactor;
a source of the radiant heat thermally coupled to the ultra-high heat flux chemical reactor, where the source of the radiant heat energy is one or more of 1) gas-fired burners, 2) nuclear power, 3) electric heaters and 4) any combination of these;
one or more feed lines connected into the chemical reactor in order to provide chemical reactants including particles of biomass, a steam carrier gas, and methane; and
multiple reactor tubes located inside the cavity of the thermal receiver, wherein an endothermic chemical reaction driven by the radiant heat energy occurs within the multiple reactor tubes, and wherein the particles of biomass are gasified in the presence of the steam (H2O) carrier gas and the methane (CH4) from the one or more feed lines in a simultaneous steam reformation and steam biomass gasification reaction to produce reaction products that include hydrogen and carbon monoxide gas using the radiant heat energy radiated from the inner wall and then into the multiple reactor tubes, where the operational temperature of the high heat flux driven chemical reactor is maintained at greater than 900 degrees C. by the source of radiant heat, and where the energy source for driving the endothermic chemical reaction comes from the source of the radiant heat, rather than by burning the particles of biomass itself, and where the multiple reactor tubes and cavity walls of the receiver transfer energy primarily by radiation absorption and re-radiation, rather than by convection or conduction, to reactants in the chemical reaction to drive the endothermic chemical reactions of the simultaneous steam reformation and the steam biomass gasification reaction in the reactor tubes.

2. The ultra-high heat flux chemical reactor of claim 1, wherein the ultra-high heat flux chemical reactor has a downdraft geometry with the multiple reactor tubes in a vertical orientation located inside the thermal receiver, and where the ultra-high heat flux chemical reactor is heated by two or more sets of the gas-fired burners, and a radiation driven geometry of the cavity wall of the thermal receiver relative to the reactor tubes locates the multiple tubes of the ultra-high heat flux chemical reactor as offset and in a staggered arrangement inside the receiver, where a surface area of the cavity walls is greater than an area occupied by the reactor tubes to allow the radiation to reach areas on the tubes from multiple angles, where the inner wall of the receiver cavity and the reactor tubes exchange energy primarily by the radiation, with the walls and tubes acting as re-emitters of radiation to achieve a high radiative heat flux reaching all of the tubes, and thus, avoid shielding and blocking the radiation from reaching the tubes, allowing for the reactor tubes to achieve a fairly uniform temperature profile from the start to the end of the reaction zone in the reactor tubes.

3. The ultra-high heat flux chemical reactor of claim 1, wherein a high heat flux of 100-250 kW/m^2 is achieved by radiative heat transfer through the selected material of the reactor tube walls at a high temperature of equal to or greater than 1000° degrees C. wall temperature, and a geometry of the reactor tubes and the inner wall of the cavity to shape a distribution of incident radiation with 1) staggered and offset tubes that are combined with 2) a large diameter cavity wall compared to an area occupied by the enclosed tubes, and additionally 3) combined with an inter-tube radiation exchange between the multiple reactor tube geometric arrangement relative to each other where the geometry is used to shape a distribution of incident radiation via reflection or absorption within the cavity of the thermal receiver.

4. The ultra-high heat flux chemical reactor of claim 1, where the chemical reactor is heated by two or more sets of the gas-fired burners, wherein the multiple reactor tubes making up the high heat flux chemical reactor can be made of a material, including SiC or coated graphite, that retains structural integrity at temperatures greater than 950 degrees C. and as high as 1600 degrees C., where due to the high operating temperatures in the reactor, radiation is a primary mode of heat transfer between the inner wall of the cavity and the reactor tubes, and there is also significant inter-tube and intra-tube heat transfer via the radiation and re-absorption, resulting in a high degree of circumferential and axial uniformity in the temperature of the reactor tubes, wherein this uniform temperature profile allows chemical reactions to occur consistently throughout the entire volume of the tubes, and where a temperature profile along the reactor tube is substantially constant but the heat flux is subject to large gradients compared to the temperature variation; and an entrained-flow biomass feed system that is feedstock flexible via at least particle size control of the biomass and that the source of radiant heat for the chemical reaction comes from an external source, rather than burning the biomass itself, where the entrained-flow biomass feed system supplies the biomass particles in the carrier gas to the chemical reactor.

5. The ultra-high heat flux chemical reactor of claim 1, wherein the inner wall of the cavity absorbs or highly reflects the concentrated energy from the gas-fired burners positioned along the wall of the cavity to cause energy transport by thermal radiation and reflection to generally convey the ultra-high heat flux to the biomass particles inside the walls of the reactor tubes;

a material making up the inner wall of the receiver cavity has mechanical and chemical properties to retain its structural strength at high temperatures between 1100-1600° C., have very high emissivity of $\epsilon > 0.8$ or high reflectivity of $\epsilon < 0.2$, as well as high heat capacity (>200 J/kg-K), and low thermal conductivity (<1 W/m-K) for the receiver cavity; and a material making up the reactor tubes possesses high emissivity ($\epsilon > 0.8$), high thermal conductivity (>1 W/m-K), moderate to high heat capacity (>150 J/kg-K).

6. The ultra-high heat flux chemical reactor of claim 1, wherein steam reacts with both the biomass and the methane, but the biomass and the methane do not react with each other, and wherein a steam to carbon molar ratio is in a range of 1:1 to 1:4, and the temperature is high enough that the chemical reaction occurs without the presence of a catalyst.

7. The ultra-high heat flux chemical reactor of claim 1, wherein a dry reform of the methane with CO2 either contained within natural gas or fed as a separate feedstock occurs in the chemical reactor, such that, even if some CO2 is present in the natural gas consisting mainly of the methane, the CO2 and the methane react with the high heat via dry reforming to produce hydrogen and carbon monoxide.

8. An integrated chemical plant with an ultra-high heat flux chemical reactor located inside a thermal receiver, comprising:

a cavity made of highly reflective material that distributes radiant energy, where the thermal receiver encloses multiple reactor tubes of the ultra-high heat flux chemical reactor, and where the reactor tubes are configured to pass chemical reactants including 1) methane, 2) natural gas, 3) steam, 4) biomass particles, and 5) any combination of the four to pass through a heat transfer aid to cause a steam methane reaction and a gasification reaction of the biomass particles using thermal energy from the radiant energy;

wherein the heat transfer aid is used to heat the chemical reactants, where the heat transfer aid is one or more of the following located inside each reactor tube: a fluidized bed or entrained flow of biomass particles, a fluidized bed or entrained flow of chemically inert particles, reticulate porous ceramic (RPC) foam, a ceramic monolith, ceramic tubes or aerogels, open structured packed rings including Raschig rings, gauze or wire constructed of a high temperature-resistant material, and any combination of these;

wherein radiation is a primary mode of heat transfer to the heat transfer aids and the chemical reactants from the reactor tube walls, and conduction, convection, or some combination of the two are a secondary mode of heat transfer from a wall of the cavity and the reactor tubes;

a length and diameter dimensions of a gasification reaction zone of each of the reactor tubes is sized to give a residence time of at least 0.01 second at a gasification temperature of at least 900 degrees C., and an exit of the gasification zone in the multiple reactor tubes, wherein reaction products have a temperature from the exit of the gasification zone that equals or exceeds 900 degrees C., and the multiple reactor tubes increase available reactor surface area for radiative exchange to the biomass particles, as well as inter-tube radiation exchange, where a source of the radiant heat is one or more of gas-fired burners, nuclear power, and electric heaters, and any combination of these; and wherein an operational temperature of the ultra-high heat flux chemical reactor is maintained at greater than 900 degrees C.

9. The integrated chemical plant with the ultra-high heat flux chemical reactor of claim 8, further comprising:

an inner wall of the cavity acting as a radiation distributor by 1) absorbing radiation and re-radiating to the reactor tubes, 2) reflecting incident radiation to the tubes, and 3) any combination of these, where the radiation from 1) the inner wall, 2) directly from a set of gas-fired burners, and 3) from an outside wall of other reactor tubes acting as re-emitters of radiation is absorbed by the reactor tubes, and then the heat is transferred, by conduction to an inner wall of the reactor tubes, where the heat radiates to the chemical reactants at temperatures between 900 degrees C. and 1600 degrees C., and preferably above 1100 degrees C.;

where the source of the radiant heat is the set of gas-fired burners and the gas-fired burners use recuperated waste heat to pre-heat combustion air for the gas-fired burners; and wherein a rapid gasification of dispersed falling biomass particulates with a resultant stable ash formation occurs within a residence time within a reaction zone in the reactor tubes in the at least 0.01 second, resulting in a complete amelioration of tar to less than 500 milligrams per normal cubic meter, and at least a 90% conversion of the biomass into hydrogen and carbon monoxide products.

10. The integrated chemical plant of claim 8, further comprising:

a multiple port lock hopper configured to simultaneously feed multiple feed gas entrainment lines from a single lock hopper, where the feed gas entrainment lines supply biomass particles to the multiple reactor tubes;

a torrefaction unit that is geographically located on a same site as the ultra-high heat flux chemical reactor and configured to subject the biomass to partial pyrolysis with recouped waste heat from the chemical reaction in a temperature range of up to 300 degrees C. to make the biomass 1) brittle and easier for grinding, 2) dryer, less sticky, and easier to feed in a conveying system, and 3) subject to less spoilage in storage as a torrefied biomass, and to produce off-gases from a torrefaction process, and the off-gases from a torrefaction of the biomass are used for one or more of 1) an entrainment carrier gas, 2) an energy source for steam generation, or 3) a gas for the gas-fired burners; and a quench zone immediately downstream of an exit of the ultra-high heat flux chemical reactor to immediately quench via rapid cooling of at least hydrogen and carbon monoxide of reaction products within 10 seconds of exiting the ultra-high heat flux chemical reactor to achieve a temperature after quenching of 800 degrees C. or less, which is below a level to reduce coalescence of ash remnants of the biomass particles.

11. The integrated chemical plant of claim 10, further comprising:

a grinding system having a grinding device that is at least one of 1) a mechanical cutting device, 2) a shearing device, 3) a pulverizing device, and 4) any combination of these that breaks apart the biomass, and a series of perforated filters in an entrained-flow biomass feed system, where the grinding device and perforated filters grind partially pyrolyzed biomass from a torrefaction unit to control particle size of the biomass to be between 50 um and 1000 um, where the torrefaction unit supplies the partially pyrolyzed biomass to the grinding system and the torrefaction of the partially pyrolyzed biomass reduces the energy required by the grinding device to control the particle size of the biomass; and wherein the integrated chemical plant converts the particles of biomass to gasoline as follows, the hydrogen and carbon monoxide reaction products are converted to methane in an on-site methanol synthesis plant, and then the methanol is converted to gasoline in a methanol-to-gas process.

12. The integrated chemical plant of claim 8, further comprising:

a feeding vessel of a biomass feed system that supplies a tube subset of two or more reactor tubes in the chemical reactor, where the feeding vessel has one or more outlets configured to supply a consistent volumetric amount of biomass particles within 10 percent of a demand signal amount when distributing biomass particles to the two or more reactor tubes;

a computerized control system to send a feed demand signal to the biomass feed system to control 1) an amount of reactor tube sets to be fed particles of biomass in the chemical reactor, 2) an amount of gas fired burners supplying heat, 3) a rate at which particular gas fired burners supply heat, and 4) any combination of these, based on control signals and a temperature measured for the chemical reactor;

an entrainment carrier gas system to supply carrier gas for the particles of biomass in the biomass feed system to the chemical reactor;

a flow enhancer, including a bulkmatology flow enhancer or a porous-walled tube, in the biomass feed system to control an amount of the entrainment carrier gas carrying the particles of biomass entering a gasification reaction zone of the reactor tubes by reducing a velocity of the entrainment carrier gas just prior to an entrance to the gasification reaction zone of the reactor tubes by removing a controlled portion of the entrainment carrier gas through the flow enhancer in response to a feedback signal; and an on-site chemical synthesis reactor that is geographically located on the same site as the chemical reactor and integrated to receive hydrogen and carbon monoxide products in the form of a syngas, wherein the on-site chemical synthesis reactor has an input to receive the syngas, which contains the hydrogen and carbon monoxide products from the chemical reactor, and is configured to use the syngas in a hydrocarbon synthesis process to create a liquid hydrocarbon fuel or other chemical.

13. The integrated chemical plant of claim 10, further comprising:
an exit of a gasification reaction zone in the reactor tubes of the chemical reactor, where two or more of the multiple reactor tubes form into a group at the exit and the group combines their reaction products into a reaction product syngas stream and un-reacted particles from the biomass gasification reaction into a larger pipe per group that forms a portion of the quench zone;
one or more sprayers inside the larger pipe to inject a cooling fluid directly into the reaction product syngas stream to make a temperature transition from the at least 900 degree C. to less than 500 degrees C. within 0.1-10 seconds to prevent metal dusting corrosion of the pipe walls;
a sulfur removal sorbent, present in either the biomass gasification reaction or initially introduced in the quench zone, to reduce an amount of sulfur present in the reaction product syngas stream exiting the quench zone; and
one or more hot particle filters to remove particulates from the reaction product syngas stream exiting the quench zone, wherein the particulates are sent to an ash holding vessel.

* * * * *